United States Patent
Bitfu et al.

(10) Patent No.: US 6,528,531 B1
(45) Date of Patent: Mar. 4, 2003

(54) ALIPHATIC HYDROXY SUBSTITUTED PIPERIDYL DIARYL PYRROLE DERIVATIVES AS ANTIPROTOZOAL AGENTS

(75) Inventors: Tesfaye Bitfu, Westfield, NJ (US); Danqing D. Feng, Branchburg Township, NJ (US); Gui-Bai Liang, Scotch Plains, NJ (US); Mitree M. Ponpipom, Branchburg, NJ (US); Xiaoxia Qian, New York, NY (US); Michael H. Fisher, Ringoes, NJ (US); Matthew J. Wyvratt, Mountainside, NJ (US); Robert L. Bugianesi, Brick, NJ (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/709,961

(22) Filed: Nov. 10, 2000

Related U.S. Application Data

(60) Provisional application No. 60/165,144, filed on Nov. 12, 1999.

(51) Int. Cl.$^7$ .................... A61K 31/445; C07D 211/68; C07D 401/00
(52) U.S. Cl. .................... 514/318; 514/326; 514/327; 514/352; 514/354; 546/194; 546/208; 546/210; 546/223
(58) Field of Search ................. 546/194, 208, 546/216, 223; 514/318, 326, 327, 352, 354

(56) References Cited

U.S. PATENT DOCUMENTS 5,776,954 A * 7/1998 De Lasso et al. ........... 514/340
5,792,778 A   8/1998 de Laszlo et al. .......... 514/218

OTHER PUBLICATIONS

Shimozato et al, Chemical Abstracts vol. 133. No. 335241, Preparation of 3-(pyridin-4-yl)-H-pyrrole derivatives as preventive or inhibitory agents for hepatopathy, 1999.*
Database WPI, Section Ch, Week 199309, Derwent Publications Ltd., London, GB, AN 1993-071029.
Takimoto, Chris H. and Susan G. Arbuck, "The Camptothecins", Cancer Chemotherapy and Biotherapy, 1996, Chabner, Philadelphia, pp. 463–484.
Bernacki, Ralph J. et al., "In Vitro Antitumour Activity of 9–Nitro–Camptothecin as a Single Agent and in Combination with other Antitumor Drugs", Department of Pharmacology and Therapeutics, Roswell Park Cancer Institute, Buffalo, New York, AAN, N.Y. Acad. Sci., vol. 922, 2000, pp. 293–297.
Karaberis, E. and D. Mourelatos, "Enhanced Cytogenetic and Antitumor Effects by 9–Nitrocamptothecin and Antineoplastics", Laboratory of Biology and Genetics, Medical School, Aristotle University, Thessaloniki, Greece, Teratogenesis Carcinogenesis and Mutagenesis, vol. 20, No. 3, 2000, pp. 141–146.
Dainiak, Nicholas et al., "DNA Topoisomerase Inhibitors Block Erythropoiesis and Delay Hemoglobinization In Vitro", Journal of Cellular Physiology, vol. 138, No. 1, 1989, pp. 87–96.
Drewinko, B et al., "Combination Chemo Therapy In–Vitro with Adriamycin Observations of Additive Antagonistic and Synergistic Effects When Used in 2 Drug Combinations on Cultured Lymphoma Cells", Cancer Biochemistry Biophysics, vol. 1, No. 4, 1976, pp. 187–195.
Kaufmann, Scott H. "Antagonism between Camptothecin and Topoisomerase II–directed Chemotherapeutic Agents in a Human Leukemia Cell Line", Cancer Research, vol. 51, No. 4, 1991, pp. 1129–1136.
Guichard, Sylvie et al., "Cellular Interactions of 5–Fluorouracil and the Camptothecin Analogue CPT–11 (Irinotecan) in a Human Colorectal Carcinoma Cell Line" Biochemical Pharmacology, vol. 55, No. 5, Mar. 1, 1998, pp. 667–676.
Ciesielski, M.J. et al., "Synergistic cytotoxicity, apoptosis and protein–linked DNA breakage by etoposide and camptothecin in human U87 glioma cells: dependence on tyrosine phosphorylation" Journal of Neuro–Oncology, 1999, 41/3, pp. 223–234.
Giovanella, B.C. et al., "Enhanced antitumor effectiveness of camptothecin (CPT) and derivatives administered by continuous infusion through scheduling and combination with DNA damaging agents." Proceedings of the American Association for Cancer Research, vol. 36, Mar. 1991, p 391.

* cited by examiner

Primary Examiner—Alan L. Rotman
Assistant Examiner—Raymond Covington
(74) Attorney, Agent, or Firm—Mollie M. Yang; David L. Rose

(57) ABSTRACT

Trisubstituted pyrroles are antiprotozoal agents useful in the treatment and prevention of protozoal diseases in human and animals, including the control of coccidiosis in poultry.

21 Claims, No Drawings

ALIPHATIC HYDROXY SUBSTITUTED PIPERIDYL DIARYL PYRROLE DERIVATIVES AS ANTIPROTOZOAL AGENTS

CROSS-REFERENCE TO RELATED APPLICATIONS

This application is a non-provisional application related to U.S. Provisional Application Serial No. 60/165,144 filed on Nov. 12, 1999 priority of which is claimed hereunder.

BACKGROUND OF THE INVENTION

Parasitic protozoa are responsible for a wide variety of infections in man and animals. Many of the diseases are life threatening to the host and cause considerable economic loss in animal husbandry. For example, malaria remains a significant health threat to humans despite massive international attempts to eradicate the disease; trypanosomiasis such as Chagas disease caused by *Trypanosoma cruzi* and African sleeping sickness caused by *T. brucei* are not uncommon in Africa and South America; and opportunistic infections in immunocompromised hosts caused by *Pneumocystis carinii, Toxoplasma gondii*, Cryptosporidium sp. are becoming increasingly significant in the developed countries.

A protozoal infection of great economic importance is coccidiosis, a widespread disease of domesticated animals produced by infections by protozoa of the genus Eimeria. Some of the most significant of Eimeria species are those in poultry namely *E. tenella, E. acervulina, E. necatrix, E. brunetti* and *E. maxima*. The disease is responsible for high levels of morbidity and mortality in poultry and can result in extreme economic losses.

In some protozoal diseases, such as Chagas disease, there is no satisfactory treatment; in others, drug-resistant strains of the protozoa may develop. Accordingly, there exists a continued need to identify new and effective anti-protozoal drugs.

U.S. Pat. No. 5,792,778 discloses compounds of the formula:

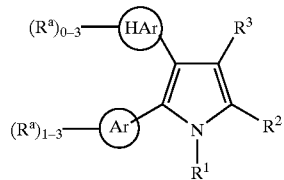

in which HAr may be 4-pyridyl, Ar may be 4-fluorophenyl, $R^2$ may be substituted 4-piperidyl and $R^3$ may be hydrogen.

SUMMARY OF THE INVENTION

The instant invention is concerned with diarylpyrrole derivatives which are useful as antiprotozoal agents. Thus, it is an object of this invention to describe such compounds. It is a further object to describe processes for the preparation of such compounds. Another object is to describe methods and compositions which use the compounds as the active ingredient thereof. Further objects will become apparent from reading the following description.

DETAILED DESCRIPTION OF THE INVENTION

The present invention provides compounds of formula I:

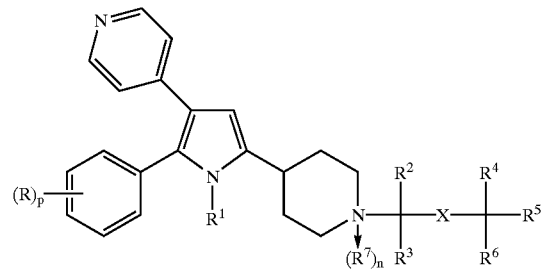

or a physiologically acceptable salt thereof,
wherein
n is 0 or 1;
m is 0, 1 or 2;
p is 1, 2 or 3;
X is
  (1) a bond,
  (2) $(CR^aR^a)_p$,
  (3) $C_{3-7}$ cycloalkylene, or
  (4) $C_{3-7}$ cycloalkylidene;
R is halogen;
$R^1$ is
  (1) hydrogen or
  (2) $C_{1-6}$ alkyl;
$R^2$ and $R^3$ are independently selected from
  (1) hydrogen,
  (2) $C_{1-6}$alkyl optionally substituted with $OR^b$,
  (3) $C_{2-6}$alkenyl,
  (4) $C_{2-6}$alkynyl,
  (4) phenyl optionally substitued with $OR^b$,
  (5) benzyl optionally substitued with $OR^b$,
  (6) $CO_2R^b$; or
$R^2 + R^3$ represent $=O$; or
when X is a bond or $(CR^aR^a)_p$, $R^2$ and $R^4$ together complete a 4- to 7-membered non-aromatic ring containing 1 or 2 heteroatoms independently selected from O and $S(O)_m$, and said ring being optionally substituted with 1 to 5 groups independently selected from oxo, $OR^b$, $CH_2OR^b$, $CH_2OC(O)R^b$ and $C_{1-6}$alkyl; or
when X is a bond or $(CR^aR^a)_p$, $R^2$ and $R^5$ together complete a 4- to 7-membered non-aromatic ring containing 0 to 2 heteroatoms independently selected from O and $S(O)_m$, said ring being optionally substituted with 1 to 5 groups independently selected from oxo, $OR^b$, $CH_2OR^b$, $CH_2OC(O)R^b$ and $C_{1-6}$alkyl;
$R^4$ is
  (1) $OR^b$,
  (2) $OC(O)R^b$,
  (3) $OC(O)OR^b$,
  (4) $OC(O)(CH_2)_mNR^bR^b$,
  (5) $OSO_2R^b$,
  (6) $S(O)_mR^b$
  (7) $OP(O)(OR^b)_2$, or
  (8) $CO_2R^b$; or
$R^4 + R^6$ represent $=O$; or
$R^4$, $R^5$ and the carbon atoms to which they are attached form a 3- to 7-membered non-aromatic ring containing 1 or 2 heteroatoms independently selected from O or $S(O)_m$, said ring being optionally substituted with 1 to 5 groups independently selected from oxo, $OR^b$, $CH_2OR^b$, $CH_2OC(O)R^b$ and $C_{1-6}$alkyl; or $R^5$ and $R^6$ are independently selected from
(1) hydrogen,
(2) $C_{1-12}$alkyl,
(3) $C_{2-12}$alkenyl,
(4) $C_{2-12}$alkynyl,
(5) $C_{3-7}$cycloalkyl-$(C_{1-6}$alkyl$)_n$,
(6) mono-, bi- or tricyclic heterocyclyl-$(C_{1-6}$alkyl$)_n$, wherein said heterocyclyl contains 3 to 12 ring atoms 1 to 4 of which are independently selected from O and $S(O)_m$,
(7) aryl-$(C_{1-6}$alkyl$)_n$,
(8) heteroaryl-$(C_{1-6}$alkyl$)_n$,
(9) $CO_2R^b$, or
(10) $OR^b$, wherein alkyl, alkenyl and alkynyl are optionally substituted with 1 to 5 groups independently selected from $R^c$, cycloalkyl and heterocyclyl are optionally substituted with 1 to 5 groups independently selected from $R^c$, alkyl, and spirofused $C_{3-6}$ cycloalkylidene, and aryl and heteroaryl are optionally substituted with 1 to 3 groups independently selected from $R^d$, or $R^5$, $R^6$ and the carbon atoms to which they are attached form a 3- to 7-membered non-aromatic ring containing 0 to 2 heteroatoms independently selected from O and $S(O)_m$, optionally substituted with 1 to 5 groups independently selected from oxo, $OR^b$, $CH_2OR^b$, $CH_2OC(O)R^b$ and $C_{1-6}$alkyl; or when X is $(CR^aR^a)_p$, $R^5$ and any one of the $R^a$ may together complete a 3- to 7-membered non-aromatic carbocyclic ring;

$R^7$ is
(1) O or
(2) methyl;

$R^a$ is
(1) hydrogen, or
(2) $C_{1-6}$alkyl, or $R^b$ is
(1) hydrogen,
(2) $C_{1-12}$alkyl
(3) $C_{2-12}$alkenyl,
(4) $C_{2-12}$alkynyl,
(5) $C_{3-7}$cycloalkyl-$(C_{1-6}$alkyl$)_n$,
(6) heterocyclyl-$(C_{1-6}$alkyl$)_n$,
(7) aryl-$(C_{1-6}$alkyl$)_n$, or
(8) heteroaryl-$(C_{1-6}$alkyl$)_n$, wherein alkyl, cycloalkyl, heterocyclyl, alkenyl and alkynyl are optionally substituted with up to 5 groups independently selected from $R^c$, and aryl and heteroaryl are optionally substituted with up to 3 groups independently selected from $R^d$, or two $R^b$ groups attached to the same nitrogen atom together complete a 4- to 7-membered ring optionally containing an additional heteroatom selected from O, S and N—Rf;

$R^c$ is
(1) halogen,
(2) $S(O)_mR^e$,
(3) $OR^e$,
(4) $OC(O)NR^eR^e$,
(5) $OC(O)OR^e$,
(6) $OC(O)R^e$,
(7) $OSO_2R^e$
(8) $OCF_3$,
(9) $CF_3$,
(10) $C(O)OR^e$
(11) $C(O)R^e$
(12) oxo,
(13) $N_3$,
(14) CN,
(15) $NO_2$, or
(16) $P(O)(OR^e)_2$;

$R^d$ is
(1) a group selected from $R^c$,
(2) $C_{1-6}$alkyl optionally substituted with 1 to 6 groups selected from $R^c$,
(3) aryl optionally substituted with 1 to 3 groups selected from $R^c$,
(4) heteroaryl optionally substituted with 1 to 3 groups selected from $R^c$,
(5) $NR^eR^e$,
(6) $NR^fSO_2R^e$,
(7) $NR^fC(O)OR^e$,
(8) $NR^fC(O)R^e$,
(9) $NR^fC(O)NR^eR^e$;

$R^e$ is
(1) hydrogen,
(2) $C_{1-2}$alkyl optionally substituted with 1 to 5 groups selected from halogen, CN, OH and $C_{1-10}$alkoxy optionally substituted with oxiranyl, hydroxy or $C_{1-6}$ alkyl,
(3) $C_{2-12}$alkenyl,
(4) $C_{2-12}$alkynyl,
(5) $C_{3-7}$cycloalkyl-$(C_{1-6}$alkyl$)_n$,
(6) aryl($C_{1-6}$alkyl$)_n$ optionally substituted with $NO_2$, $C_{1-6}$alkyl, $C_{1-6}$alkoxy, or halogen,
(7) heteroaryl$(C_{1-6}$alkyl$)_n$, or two $R^e$ groups together with the nitrogen atom to which they are attached form a 3- to 7-membered ring optionally containing an additional heteroatom selected from O, S and N—Rf;

$R^f$ is
(1) hydrogen or
(2) $C_{1-6}$alkyl.

In one subset of compouds of formula I R is 4-fluoro.

In another subset of compounds of formula I $R^1$ is hydrogen.

In another subset of compounds of formula I n of $(R^7)_n$ is 0.

In another subset of compouds of formula I $R^3$ is hydrogen, and $R^2$ is hydrogen, methyl, hydroxy methyl, $C_{1-3}$alkoxy methyl, phenyl, or $C_{1-3}$alkoxyphenyl; or when X is a bond or $(CR^aR^a)_p$, $R^2$ and $R^4$ together complete a 4- to 7-membered non-aromatic ring containing 1 or 2 heteroatoms independently selected from O and $S(O)_m$, and said ring being optionally substituted with 1 to 5 groups independently selected from oxo, $OR^b$, $CH_2OR^b$, and $C_{1-6}$alkyl; or when X is a bond or $(CR^aR^a)_p$, $R^2$ and $R^5$ together complete a 4- to 7-membered non-aromatic ring containing 0 to 2 heteroatoms independently selected from O and $S(O)_m$, said ring being optionally substituted with 1 to 5 groups independently selected from oxo, $OR^b$, $CH_2OR^b$, and $C_{1-6}$alkyl.

In another subset of compounds of formula I X is a bond, $(CR^aR^a)_p$ wherein p is 1 or 2, or $C_{3-6}$cycloalkylene. Examples of X being $(CR^aR^a)_p$ include $CH(CH_3)$, $CH_2CH_2$, $CH_2$, $CH(CH_2CH_3)$, $C(CH_3)_2$ and the like.

In another subset of compounds of formula I $R^4$ is $OR^b$, or $R^4$ and $R^6$ together represent oxo, or $R^4$, $R^5$ and the carbon atoms to which they are attached form a 3- to 7-membered non-aromatic ring containing 1 or 2 heteroatoms independently selected from O or $S(O)_m$, said ring being optionally substituted with 1 to 5 groups independently selected from oxo, $OR^b$, $CH_2OR^b$, and $C_{1-6}$alkyl.

In another subset of compounds of formula I $R^5$ and $R^6$ are each hydrogen or $C_{1-12}$ alkyl optionally substituted with 1 to 5 groups independently selected from $R^c$; or $R^6$ is hydrogen and $R^5$ is selected from $C_{1-12}$alkyl, $C_{3-6}$cycloalkyl-$(C_{1-3}$alkyl$)_n$, heterocyclyl-$(C_{1-3}$alkyl$)_n$, wherein said heterocyclyl contains 3 to 6 ring atoms 1 to 2 of which are independently selected from O and $S(O)_m$, aryl-$(C_{1-3}$alkyl$)_n$, heteroaryl-$(C_{1-3}$alkyl$)_n$, $CO_2R^b$, and $OR^b$, wherein alkyl, alkenyl and alkynyl are optionally substituted with 1 to 5 groups independently selected from $R^c$, cycloalkyl and heterocyclyl are optionally substituted with 1 to 5 groups independently selected from $R^c$ and alkyl, and aryl and heteroaryl are optionally substituted with 1 to 3 groups independently selected from $R^d$; or $R^5$, $R^6$ and the carbon atoms to which they are attached form a 3- to 7-membered non-aromatic ring containing 0 to 2 heteroatoms independently selected from O and $S(O)_m$, optionally substituted with 1 to 5 groups independently selected from oxo, $OR^b$, $CH_2OR^b$, and $C_{1-6}$alkyl; or when X is $(CR^aR^a)_p$, $R^5$ and any one of the $R^a$ may together complete a 3- to 7-membered non-aromatic carbocyclic ring.

Compounds of formua Ia represent one embodiment of formula I:

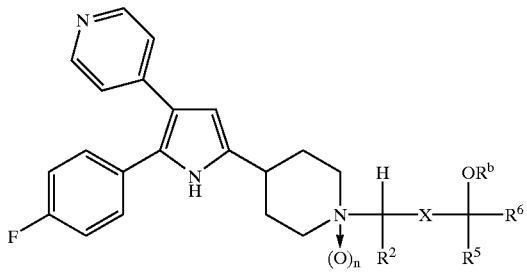

Ia wherein n, X, $R^2$, $R^5$, $R^6$ and $R^b$ are as defined under formula I. In a subset of formula Ia $R^2$ is selected from hydrogen, $C_{1-3}$alkyl optionally substituted with hydroxy or $C_{1-3}$alkoxy, and phenyl optionally substituted with $C_{1-3}$alkoxy. In another subset of formula Ia, X is a bond, $(CR^aR^a)_p$ or $C_{3-6}$alkylene in which $R^a$ is H or $C_{1-3}$ alkyl, and p is 1 or 2. In another subset of formula Ia $R^5$ is hydrogen, $C_{1-6}$alkyl, $CO_2R^b$, aryl, heteroaryl, or heterocyclyl wherein alkyl, aryl, heteroaryl and heterocyclyl are optionally substituted with 1 to 5 groups selected from $OR^b$ and halogen, or $R^5$, $R^6$ and the carbon atom to which they are attached for a $C_{3-6}$ carbocyclic ring, or when X is a bond or $(CR^aR^a)_p$, $R^5$ and $R^2$ together complete a 4- to 5-membered non-aromatic ring containing 0 or 1 heteroatom selected from O and $S(O)_m$, or when X is $(CR^aR^a)_p$, $R^5$ and one of the $R^a$ together complete a 3- to 6-memebered carbocyclic ring.

In another subset of compounds of formula Ia are compounds of formula Ib:

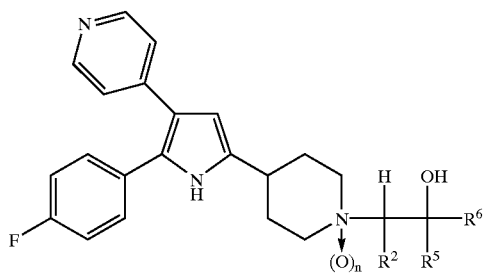

Ib wherein $R^6$ is hydrogen, $R^5$ is $C_{1-6}$ alkyl, $C_{2-10}$alkenyl, $CO_2R^b$, aryl, heteroaryl or heterocyclyl wherein alkyl, alkenyl, aryl, heteroaryl and heterocyclyl are optionally substituted with 1 or 2 groups selected from $OR^b$ and halogen, or $R^5$, $R^6$ and the carbon atom to which they are attached form a $C_{3-6}$ carbocyclic ring, or $R^5$ and $R^2$ together complete a 4- to 5-membered non-aromatic ring containing 0 or 1 heteroatom selected from O and $S(O)_m$.

In one subset of formula Ib $R^5$ is selected from
(1) $C_{1-6}$ alkyl optionally substituted with 1 or 2 groups selected from (a) hydroxy, (b) $C_{1-10}$alkoxy optionally substituted with 1 to 10 halogen atoms or cyano, (c) $C_{3-6}$alkenyloxy, (d) heteroaryl-$C_{1-3}$alkoxy, (e) phenoxy optionally substituted with 1 or 2 groups selected from nitro, $C_{1-5}$alkoxy, halogen, and $C_{1-5}$alkyl, (f) benzyloxy, and (g) halogen
(2) $CO_2$—$C_{1-3}$alkyl,
(3) $C_{2-10}$alkenyl, and
(4) phenyl optionally substituted with 1 or 2 groups selected from (a) nitro, (b) $C_{1-5}$alkoxy optionally substituted with 1 to 5 halogen atoms, (c) halogen, (d) amino, (e) mono-$C_{1-5}$alkylamine, (f) di-$C_{1-5}$alkylamine, (g) trifluoromethyl, and (h) $C_{1-5}$alkyl.

In another subset of formula Ib $R^2$ and $R^5$ together complete a 4- to 7-membered non-aromatic ring containing 0 to 2 heteroatoms independently selected from O and $S(O)_m$, said ring being optionally substituted with 1 to 5 groups independently selected from oxo, $OR^b$, $CH_2OR^b$, $CH_2OC(O)R^b$ and $C_{1-6}$alkyl. In one embodiment of this subset the ring is selected from cyclopentane, cyclohexane, cyclopentene, tetrahydrofuran, tetrahydrothienyl and oxide and sulfoxide thereof, each of which is optionally substituted as described above.

As used herein, unless otherwise defined or limited, the following definitions apply:

"Alkyl" includes straight or branched carbon chains of the designated length. Exemplary of such alkyl groups are methyl, ethyl, propyl, isopropyl, butyl, sec-butyl, tertiary butyl, pentyl, isopentyl, hexyl, isohexyl, and the like.

"Alkenyl" includes straight and branched carbon chains of the designated length having at least one carbon-carbon double bond. Examples of alkenyl group include vinyl, allyl, 1-propenyl, 2-propenyl, isobutylenyl, hexenyl, hexadienyl, octenyl, and the like.

"Alkynyl" includes straight and branched carbon chains of the designated length having at least one carbon-carbon triple bond. Examples of alkynyl group include ethynyl, propargyl, 1-butynyl, 2-butynyl, 3-butynyl, 4-pentynyl, and the like.

The term "cycloalkylene" is a carbocyclic ring with the designated number of ring carbon atoms represented as:

Non-limiting examples of cycloalkylene include 1,2-cyclopropyl, 1,3-cyclobutyl, 1,3-cyclopentyl, 1,4-cyclohexyl, and the like.

The term "cycloalkylidene" is a carbocyclic ring with the designated number of ring carbon atoms represented as:

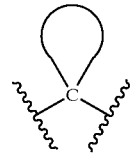

Non-limiting examples include 1,1-cyclopropylidene, 1,1-cyclobutylidene, 1,1-cyclopentylidene, 1,1-cyclohexylidene and the like.

The term "halogen" is intended to include the halogen atoms fluorine, chlorine, bromine and iodine.

The term "aryl" is an aromatic mono- or bicyclic carbocycle having from 6 to 10 carbon atoms, optionally fused to a 4- to 6-membered non-aromatic ring containing 0–3 heteroatoms selected from N, O and $S(O)_m$. Examples include phenyl methylenedioxyphenyl and naphthyl.

"Heteroaryl" is a mono-or bicyclic aromatic ring containing from 1 to 6 heteroatoms independently selected from N, O and $S(O)_m$ wherein each ring has five or six ring atoms. Examples of heteroaryl include pyridyl, pyrimidinyl, pyrrolyl, furyl, thienyl, imidazolyl, thiazolyl, thiadiazolyl, triazolyl, tetrazolyl, oxadiazolyl, oxazolyl, imidazolidinyl, pyrazolyl, isoxazolyl, benzothiadiazolyl, indolyl, indolinyl, benzodioxolyl, benzodioxanyl, benzothiophenyl, benzofuranyl, benzimidazolyl, benzisoxazolyl, benzothiazolyl, quinolinyl, benzotriazolyl, benzoxazolyl, purinyl, furopyridine and thienopyridine.

"Heterocycle" is a 3- to 7-membered non-aromatic ring containing 1–4 heteroatoms selected from N, O and $S(O)_m$, which may be optionally fused to a benzene ring. Examples of heterocycle include oxiranyl, aziridinyl, azetidinyl, oxetanyl, tetrahydrofuranyl, tetrahydropyranyl, tetrahydrothienyl including sulfoxide and sulfones thereof, 2,3- and 2,5-dihydrofuranyl, 1,3-dioxanyl, 1,3-dioxolanyl, pyrrolidinyl, imidazolinyl, imidazolidinyl, piperidinyl, morpholinyl, thiomorpholinyl, piperazinyl, benzoxazinyl,. 2,3-dihydrobenzofuranyl 1,2,3,4-tetrahydroisoquinolinyl, 1,2,3,4-tetrahydroquinolinyl.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I as individual isomers as well as mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed within compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of the general Formula I may be obtained by stereospecific synthesis using optically pure starting materials or reagents of known configuration.

The term "physiologically acceptable salts" refers to salts prepared from non-toxic bases or acids that are physiologically acceptable to the host. When the compound of the present invention is acidic, salts may be prepared from physiologically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. In one embodiment the salts are selected from ammonium, calcium, magnesium, potassium and sodium salts. Salts derived from physiologically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from physiologically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. In one embodiment acids are selected from citric, hydrobromic, hydrochloric, maleic, phosphoric, sulfuric, and tartaric acids.

Compounds of the present invention may be prepared using a variety of organic synthesis methodologies well known in the art. Examples of suitable procedures are described in the following schemes.

SCHEME 1

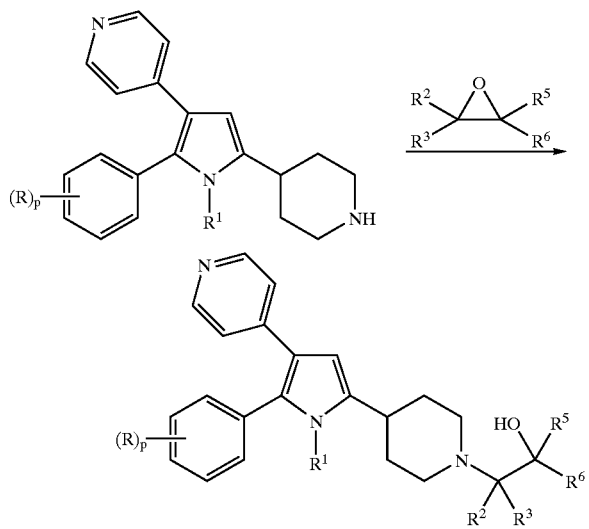

In Scheme 1, the secondary amine is treated with a suitably substituted epoxide in solvents such as methanol, methanol/methylenechloride at temperatures ranging from ambient to reflux temperature to give the desired hydroxy amines.

SCHEME 2

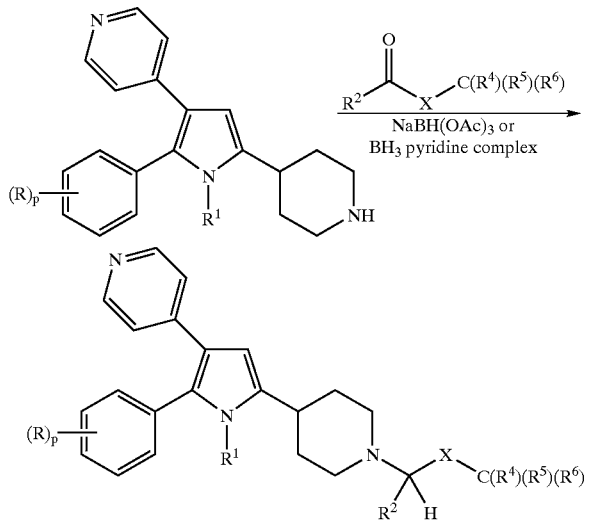

Alkylation of the piperidine nitrogen atom may be carried out by reductive amination. The reaction is carried out by treating the piperidine compound with a ketone or an aldehyde in the presence of BH₃ pyrdine complex or sodium triacetoxyborohydride to give the desired alkylated piperidines.

SCHEME 3

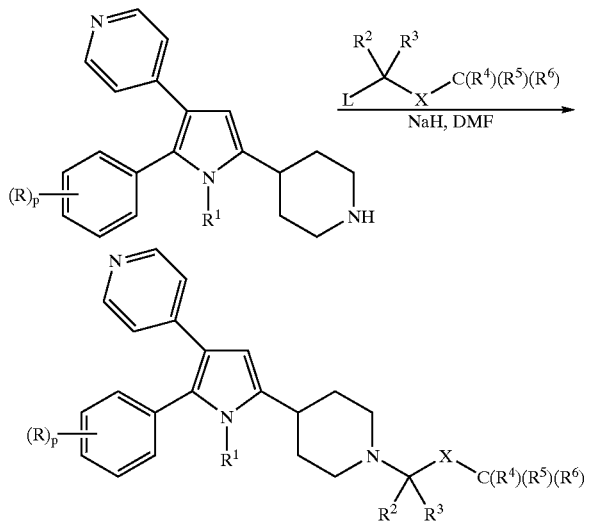

where L is a leaving group such as bromide, chloride, iodide

Scheme 3 depicts another method for the alkylation of the piperidine nitrogen atom. The piperidine compound is treated with a strong base such as sodium hydride in solvent such as DMF followed by alkyl halide, such as alkyl iodide, to give the desired tertiary amines.

SCHEME 4

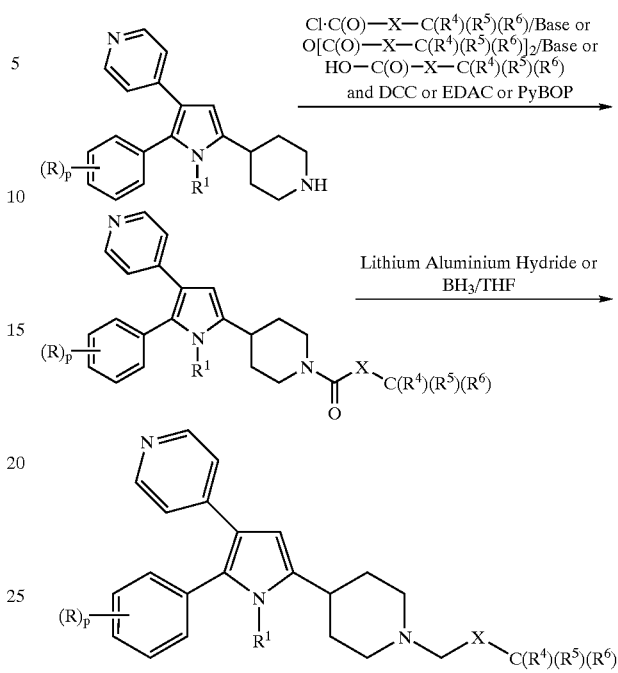

The acylation of the piperidine amine is depicted in Scheme 4. Acylation may be conveniently carried out using an acylating agent such as an acid chloride, acid anhydride, or a carboxylic acid in the presence of a coupling agent such as dicyclohexylcarbodiimide. The resulting amide may be reduced using for example a borane reagent lithium aluminum hydride and the like to provide the corresponding tertiary amine.

N-oxides are prepared by treating the amine in dichlormethane with one equivalent of m-chloroperbenzoic acid, treatment with sodium bicarbonate to remove acid and final purification of N-oxide by prep TLC on silica plate eluted with H4OH/methanol/dichlormethane 1:9:90.

In some cases, the products from the reactions described in Schemes 1 to 4 may be further modified, for example, by the removal of protecting groups or the further elaboration of free amino or hydroxy groups. These manipulations may include, but are not limited to, reduction, oxidation, alkylation, acylation, and hydrolysis reactions, which are commonly known to those skilled in the art.

Utility

The diaryl pyrroles of the present invention are useful as antiprotozoal agents. As such, they may be used in the treatment and prevention of protozoal diseases in human and animals, including poultry. Examples of protozoal diseases against which compounds of formula I may be used, and their respective causative pathogens, include: 1) amoebiasis (Dientamoeba sp., *Entamoeba histolytica*); 2) giardiasis (*Giardia lamblia*); 3) malaria (Plasmodium species including *P. vivax, P. falciparum, P. malariae* and *P. ovale*); 4) leishmaniasis (Leishmania species including *L. donovani, L. tropica, L. mexicana,* and *L. braziliensis*); 5) trypanosomiasis and Chagas disease (Trypanosoma species including *T. brucei, T. theileri, T. rhodesiense, T. gambiense, T. evansi, T. equiperdum, T. equinum, T. congolense, T. vivax* and *T. cruzi*); 6) toxoplasmosis (*Toxoplasma gondii*); 7) babesiosis (Babesia sp.); 8) cryptosporidiosis (Cryptosporidium sp.); 9) dysentery (*Balantidium coli*); 10) vaginitis (Trichomonas species including *T.vaginitis,* and *Tritrichomonas foetus*);

11) coccidiosis (Eimeria species including *E. tenella, E. necatrix, E. acervulina, E. maxima* and *E. brunetti, E. mitis, E. bovis, E. melagramatis*, and Isospora sp.); 12) enterohepatitis (*Histomonas gallinarum*), and 13) infections caused by Anaplasma sp., Besnoitia sp., Leucocytozoan sp., Microsporidia sp., Sarcocystis sp., Theileria sp., and *Pneumocystis carinii*.

Dose Range

Compounds of formula I may be administered to a host in need of treatment in a manner similar to that used for other antiprotozoal agents; for example, they may be administered parenterally, orally, topically, or rectally. The dosage to be administered will vary according to the particular compound used, the infectious organism involved, the particular host, the severity of the disease, physical condition of the host, and the selected route of administration; the appropriate dosage can be readily determined by a person skilled in the art. For the treatment of protozoal diseases in humans, the oral dosage may range from 1 mg/kg to 1000 mg/kg; and the parenteral dosage may range from 0.5 mg/kg to 500 mg/kg. For veterinary therapeutic use, the oral dosage may range from 1 mg/kg to 1000 mg/kg; and the parenteral dosage may range from 0.5 mg/kg to 500 mg/kg. For prophylactic use in humans, the oral dosage may range from 1 mg/kg to 1000 mg/kg; and the parenteral dosage may range from 0.5 mg/kg to 500 mg/kg. For prophylactic use in animal, the oral dosage may range from 1 mg/kg to 1000 mg/kg; and the parenteral dosage may range from 0.5 mg/kg to 500 mg/kg. For use as an anticoccidial agent, particularly in poultry, the compound is may be administered in the animals' feed or drinking water in accordance with common practice in the pountry industry as described below.

Composition

The compositions of the present invention comprises a compound of formula I and an inert carrier. The compositions may be in the form of pharmaceutical compositions for human and veterinary usage, or in the form of feed composition for the control of coccidiosis in poultry.

The pharmaceutical compositions of the present invention comprise a compound of formula I as an active ingredient, and may also contain a physiologically acceptable carrier and optionally other therapeutic ingredients. The compositions include compositions suitable for oral, rectal, topical, and parenteral (including subcutaneous, intramuscular, and intravenous) administrations, although the most suitable route in any given case will depend on the particular host, and nature and severity of the conditions for which the active ingredient is being administered. The pharmaceutical compositions may be conveniently presented in unit dosage form and prepared by any of the methods well-known in the art of pharmacy.

In practical use, compounds of formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, compounds of formula I may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5–10% by weight of the compound, in sufficient quantities to produce a cream or ointment having the desired consistency.

Pharmaceutical compositions suitable for rectal administration wherein the carrier is a solid may be presented as unit dose suppositories. Suitable carriers include cocoa butter and other materials commonly used in the art, and the suppositories may be conveniently formed by admixture of the combination with the softened or melted carrier(s) followed by chilling and shaping molds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

For use in the management of coccidiosis in poultry, a compound of formula I may be conveniently administered as a component of a feed composition. Suitable poultry feed composition will typically contain from about 1 ppm to about 1000 ppm, or from about 0.0005% to about 0.05% percent, by weight of a compound of formula I. The optimum levels will naturally vary with the species of Eimeria involved, and can be readily determined by one skilled in the art.

In the preparation of poultry feed, a compound of formula I may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuff include molasses, fermentation residues, corn meal, ground and rolled oats, wheat shorts and middlings, alfalfa, clover and meat scraps, together with mineral supplements such as bone meal, calcium carbonate and vitamins.

When the compound according to the present invention is used as an additive to the feed, it is typically incorporated into a "premix." The premix contains the active agent or agents as well as physiologically acceptable carriers and feedstuffs. The premix is relatively concentrated and is adapted to be diluted with other carriers, vitamin and mineral supplements, and feedstuffs to form the final animal feed. Premixes which are intermediate in concentration of active agent between a first premix and the final animal feed are sometimes employed in the industry and can be used in implementing the present invention. When employing the present compound as sole active agent, a premix desirably contains the agent at a concentration of from 0.1 to 50.0% by weight. Preferred premixes will generally contain the present compound at a concentration of from 0.5 to 25.0%, by weight. The identity of the other components of the premix and ultimate animal feed is not critical. In final feeds, the concentration of the active agent is not critical and will depend on various factors known to those skilled in the art. Such factors include the relative potency of the particular active agent and the severity of the coccidial challenge. In general, a final feed employing compound of the present invention as the sole anticoccidial will contain from about 0.0005 to about 0.05% by weight of said compound, preferably from about 0.0005 to about 0.005%.

Compositions containing a compound of formula I may also be prepared in powder or liquid concentrate form. In accordance with standard veterinary formulation practice, conventional water soluble excipients, such as lactose or sucrose, may be incorporated in the powders to improve their physical properties. Thus one embodiment of suitable powders of this invention comprises 50 to 100% w/w, and for example 60 to 80% w/w of the compound and 0 to 50% w/w and for example 20 to 40% w/w of conventional veterinary excipients. These powders may either be added to animal feedstuff, for example by way of an intermediate premix, or diluted in animal drinking water.

Liquid concentrates of this invention suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The present invention contemplates using a compound of formula (I) as sole anticoccidial agent as well as in combination with one or more other anticoccidial agents. Suitable anticoccidials for combination use include, but are not limited to, amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril. When used in combination with one or more other anticoccidial agent, the compound of formula (I) may be administered at or lower than the effective doses when used alone; for example, the final feed may contain about 0.0001 to about 0.02% by weight, or preferably from about 0.0005 to about 0.005% of a compound of formula (I). Similarly, the second anticoccidial agent in the combination may be used in an amount at or lower than those commonly used as a sole anticoccidial. The combination may be formulated into medicament for poultry use as described previously.

The formulated medicament may contain, in addition to anticoccidial agent(s) other therapeutic or nutritional agents commonly administered to poultry in the feed or drinking water; such other agents may be, for example, parasiticides, antibacterials, and growth promoters.

Anticoccidiosis Assay

One-day-old White Leghorn chickens are obtained from a commercial hatchery and acclimated in a holding room. At three days of age the test animals are selected by weight, wingbanded, and randomly placed on medicated or control diets for the duration of the experiment. One or two replicates of two birds are utilized per treatment. Following 24 h premedication, in each replicate one bird is infected with *Eimeria acervulina*, the other bird is infected with *E. tenella*. Both strains of Eimeria are sensitive to all anticoccidial products, and have been maintained in laboratory conditions for over 25 years. The inocula consist of sporulated oocysts in tap water suspensions, administered at a dose rate of 0.25 ml per bird. The inocula levels are selected by previous dose titrations to provide a low to moderate level of infection. The *E. acervulina* portion of the experiment is terminated on Day 5, the *E. tenella* on Day 6 post infection. The measured parameters are weight gain, feed consumption and oocyst production. *E. tenella* lesion scores are also recorded for background information. Treatments which provide at least 80% reduction in oocyst production are considered active, those with 50–79% are considered partially active, and those with <50% are considered inactive. The same numerical categories in weight gain and feed consumption differentiate among treatments with good, fair or poor productivity.

REFERENCE EXAMPLE 2-(4-fluorophenyl)-5-(piperidin-4-yl)-3-(4-pyridinyl)-pyrrole

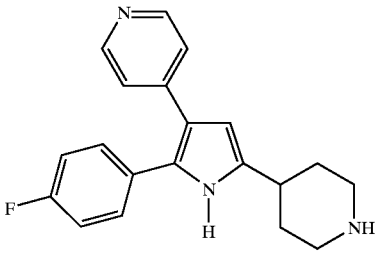

Step 1. 1-(4-fluorophenyl)-2-(4-pyridinyl)-ethanone

To a solution of lithium diisopropyl amide (2.0 M in heptane, tetrahydrofuran, ethyl benzene) 3.1 mL (6.3 mmol) in 6 mL of anhydrous tetrahydrofuran at −78° C. under nitrogen was added 0.5 g (5.3 mmol) of 4-picoline dropwise. The reaction mixture was stirred for 20 minutes and then treated with a solution of 0.9 g (5.3 mmol) of 4-fluoro-(N-methyl-N-methoxy)-benzamide in tetrahydrofuran. The reaction mixture was warmed to 0° C. and quenched by addition of 10 mL of brine. The mixture was extracted with ethyl acetate (3×10 mL) and the combined organic phases were dried over $MgSO_4$. The mixture was filtered and the filtrate was concentrated in vacuo to give the title compound as an orange solid. $H^1$ NMR ($CDCl_3$ 300 MHz): 4.23 s (d, 2H), 7.1–7.18 m (4H), 8.02 (dd, 2H), 8.55 (dd, 2H).

Step 2. 4-(1-benzyloxycarbonylpiperidin-4-yl)-2-(4-pyridyl)-1-(4-fluoro-phenyl)butane-1,4-dione To a solution of the product of Step 1 (0.5 g (2.3 mmol)) in 5.0 ml of dry dimethyl sulfoxide was added 2.4 ml (2.4 mmol) of a 1M solution of sodium hexamethyldisilazide in tetrahydrofuran. After 10 minutes, a solution of 0.72 g (2.4 mmol) of 4-(2-iodoacetyl)-1-(benzyloxycarbonyl)piperidine was added in 1 ml dimethyl sulfoxide dropwise. The reaction mixture was stirred for 2 hours, diluted with ethyl acetate (EtOAc, 20 ml) and washed with water (3×10 ml). The combined organic phases were washed with brine and dried over $MgSO_4$. The mixture was filtered and the filtrate was concentrated in vacuo. The residue was purified by MPLC over silica gel eluting with 2% $MeOH/CH_2Cl_2$ to give the desired product. FAB ms: C28H27N2O4F:474; Observed: 475 ($M^+$+1).

Step 3. 2-(4-fluorophenyl)-5-(1-benzyloxycarbonylpiperidin-4-yl)-3-(4-pyridinyl)pyrrole The product of Step 2 was heated in 5 ml of acetic acid in the presence of 2.0 g ammonium acetate at 110° C. for 1.5 hours. The reaction mixture was diluted with EtOAc (10 mL) and washed with water. The combined organic phases were washed with brine and dried over $MgSO_4$. The mixture was filtered and the filtrate was concentrated in vacuo. The residue was purified by MPLC over silica gel eluting with 2% $MeOH/CH_2Cl_2$ to give the desired product. $H^1$-NMR ($CDCl_3$, 300 MHz):1.67 (m, 2H); 2.02 (bd, 2h); 2.75–3.0 (m, 3H); 4.29 bd, 2H); 5.12 (s, 2H); 6.19 (d, 1H); 7.03 (t, 2H); 7.18 (dd, 2H); 7.25–7.39 (m, 6H); 8.39 (dd, 2H); 8.52 (bs, 1H).

FAB ms: C28H26N3O2F:455; Observed: 456 ($M^+$+1).

Step 4. 2-(4-fluorophenyl)-5-(piperidin-4-yl)-3-(4-pyridinyl)pyrrole acetate salt The product of Step 3 (183 mg) was dissolved in 5 ml of acetic acid. The solution was hydrogenated over 25 hours at atmospheric pressure in the presence of 10 mg of 10% Pd/C. The mixture was filtered and the filtrate was concentrated in vacuo to give the product. FAB ms: $C_{20}H_{20}N_3F$:321; Observed: 322 ($M^+$+1).

The following examples are provided to more fully illustrate the invention and are not to be construed as limiting the scope of the invention in any manner. In the general procedures, reaction conditions such as temperature, time, solvent may be varied depending on the reagents used, products to be made, etc. The selection of such variables are within the skills of a person having ordinary skill in the art.

Compounds exemplified below are of the general formula

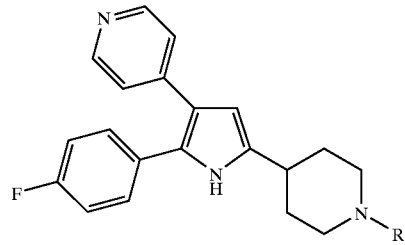

In the examples only the N—R portion is depicted. The term BOC stands for t-butyloxycarbonyl, and Ac stands for acetyl.

NMR data are collected on a Varian XL400 spectrometer. Compounds were dissolved in $CDCl_3$ or $CDCl_3$ containing 1–2 drops of $CD_3OD$, unless otherwise specified.

EXAMPLE 1

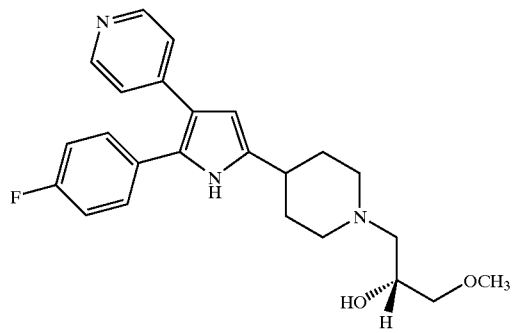

To a stirred solution of the compound of reference example (1.0 g, 3.1 mmol) in methanol (2.5 mL) and dichloromethane (20 mL) was added (R)-glycidyl methyl ether (300 mg, 3.4 mmol, 1.1 eq). The reaction mixture was stirred at 25–60° C. for 1–3 days, and then was separated either by silica gel column chromatography or by preparative thin layer chromatography, eluted with 5–10% methanol in dichloromethane. The product (0.5 g) was isolated as off-white crystalline solid as the free base.

$^1H$ NMR (400 MHz, $CDCl_3$+drop $CD_3OD$, ppm): δ1.8–2.7 (broad m, 9H), 3.0–3.5 (broad, 4H), 3.4 (s, 3H), 4.0 (broad 1H), 6.1 (s, 1H), 7.0 (m, 2H), 7.2 (m, 2H), 7.3 (m, 2H), 8.3 (m, 2H).

The procedure described in Example 1 was followed for the preparation of the following compounds:

TABLE 1

[Structure: 3-(pyridin-4-yl)-2-(4-fluorophenyl)-5-(1-R-piperidin-4-yl)-1H-pyrrole]

| Ex. | N—R | Epoxide | ¹H NMR (400 MHz, CDCl₃, ppm) |
|---|---|---|---|
| 2 | —N(CH₂CH(OH)CH₃) | propylene oxide | 1.1(d, J=6.1Hz, 3H), 1.8–2.7 (broad m, 9H), 3.0(broad, 1H), 3.2(broad, 1H), 3.9(broad 1H), 6.2(d, J=2.6Hz, 1H), 7.0(m, 2H), 7.2(m, 2H), 7.3(m, 2H), 8.4(m, 2H). |
| 3 | —N(CH₂CH(OH)CH₂OCH₂CH=CH₂) | glycidyl allyl ether | 1.8–2.8(broad m, 9H), 3.0–3.2 (broad, 2H), 3.5(m, 2H), 4.0(m 3H), 5.2(m, 2H), 5.9(m, 1H), 6.2(d, J=2.9Hz, 1H), 7.0(m, 2H), 7.2(m, 2H), 7.3(m, 2H), 8.2(broad 1H), 8.4(m, 2H). |
| 4 | —N(CH₂CH(OH)CH₂CH₂CH₃) | 1,2-epoxypentane | ‡0.85(t, J=6.7Hz, 3H), 1.3(m, 4H), 1.8–2.4(broad m, 7H), 2.6 (broad t, 1H), 3.0–3.3(broad, 3H), 3.8(broad 1H), 6.0(s, 1H), 7.0(m, 2H), 7.1(m, 2H), 7.3 (m, 2H), 8.2(m, 2H). |
| 5 | —N(CH₂CH(OH)CH₂Ph) | benzyloxirane | ‡1.6–3.2(broad m, 13H), 4.0 (broad 1H), 6.0(s, 1H), 7.0(m, 2H), 7.1–7.3(m, 9H), 8.2(m, 2H). |
| 6 | —N(CH₂CH(OH)(S)CH₃) | (S) propylene oxide | 1.1(d, J=6.1Hz, 3H), 1.8–2.7 (broad m, 9H), 3.0(broad, 1H), 3.2(broad, 1H), 3.9(broad 1H), 6.2(d, J=2.6Hz, 1H), 7.0(m, 2H), 7.2(m, 2H), 7.3(m, 2H), 8.4(m, 2H). |
| 7 | —N(CH₂CH(OH)CH₂CH₃) | 1,2-epoxybutane | ‡0.94(t, J=7.6Hz, 3H), 1.4(m, 2H), 1.8–2.7(broad m, 9H), 3.0 (broad, 1H), 3.2(broad, 1H), 3.7(broad 1H), 6.1(s, 1H), 7.0 (m, 2H), 7.2(m, 2H), 7.3(m, 2H), 8.3(m, 2H). |
| 8 | —N(CH₂CH(OH)(R)CH₃) | (R) propylene oxide | 1.1(d, J=6.1Hz, 3H), 1.8–2.7 (broad m, 9H), 3.0(broad, 1H), 3.2(broad, 1H), 3.9(broad, 1H), 6.2(d, J=3.0Hz, 1H), 7.0 (m, 2H), 7.2(m, 2H), 7.3(m, 2H), 8.4(m, 2H). |
| 9 | —N(CH₂CH(OH)(S)CH₂OCH₃) | (S)-glycidyl methyl ether | ‡1.8–2.7(broad m, 9H), 3.1 (broad m, 2H), 3.3(m, 2H), 3.3 (s, 3H), 3.9(broad, 1H), 6.2(s, 1H), 7.0(m, 2H), 7.2(m, 2H), 7.3(m, 2H), 8.4(m, 2H). |
| 10 | —N(CH₂CH(OH)(S)CH₂OH) | (R)-glycidol | ‡1.8–2.7(broad m, 9H), 3.1 (broad m, 2H), 3.4–3.7(m, 2H), 3.9(broad, 1H), 6.2(s, 1H), 7.0 (m, 2H), 7.2(m, 2H), 7.3(m, 2H), 8.3(m, 2H). |

TABLE 1-continued

[Structure: pyrrole core with 4-pyridyl at position 3, 4-fluorophenyl at position 2, and 1-R-piperidin-4-yl at position 5, NH at position 1]

| Ex. | N—R | Epoxide | $^1$H NMR (400 MHz, CDCl$_3$, ppm) |
|---|---|---|---|
| 11 | [N-CH$_2$-CH(OH)-CH$_2$-OCH$_2$CH$_3$] | glycidyl ethyl ether | ‡1.2(t, J=7.0Hz, 3H), 1.8–2.7 (broad m, 9H), 3.1(broad m, 2H), 3.4(m, 2H), 3.5(q, J=7.0 Hz, 3H), 3.9(broad, 1H), 6.1(s, 1H), 7.0(m, 2H), 7.1(m, 2H), 7.3(m, 2H), 8.2(m, 2H). |
| 12 | [N-CH$_2$-C(R)(OH)-CH$_2$OH] | (S)-glycidol | ‡1.8–2.7(broad m, 9H), 3.1 (broad m, 2H), 3.4–3.7(m, 2H), 3.9(broad, 1H), 6.2(s, 1H), 7.0 (m, 2H), 7.2(m, 2H), 7.3(m, 2H), 8.3(m, 2H). |
| 13 | [N-CH$_2$-CH(OH)-C(CH$_3$)(H)-C(O)CH$_3$] | 2-(1-methyl-2-oxo-propyl)-oxirane | 1.2(s, 1H), 1.7(m, 2H), 1.9(m, 2H), 2.3(s, 3H), 2.3(m, 4H), 2.4(d, J=13.5Hz, 1H), 2.6(m, 1H), 2.7(m, 1H), 2.9(d, J=13.5 Hz, 1H), 3.1(m, 1H), 4.4 (broad, 1H), 6.2(d, J=2.6Hz, 1H), 7.0(m, 2H), 7.2(m, 2H), 7.3(m, 2H), 8.1(broad, 1H), 8.4(m, 2H). |
| 14 | [N-CH$_2$-C(OH)(CH$_2$OCH$_3$)$_2$] | 3,4-dimethoxy isobutylene oxide | 1.8(broad, 2H), 2.0(m, 2H), 2.5(m, 5H), 3.0(broad, 2H), 3.3(s, 4H), 3.4(s, 6H), 4.0 (broad 1H), 6.2(s, 1H), 7.0(m, 2H), 7.2(m, 2H), 7.3(m, 2H), 8.0(broad, 1H), 8.4(m, 2H). |
| 15 | [N-CH$_2$-C(OH)(CH$_2$OCH$_3$)(CH$_2$OH)] | 3-hydroxy-methoxy isobutylene oxide | 1.6(broad, 2H), 1.8(m, 2H), 2.0(m, 2H), 2.4(m, 2H), 3.0 (m, 1H), 3.2(m, 1H), 3.3(AB q, 2H), 3.4(s, 3H), 3.6(AB q, 2H), 6.2(d, J=2.8Hz, 1H), 7.0 (m, 2H), 7.2(m, 2H), 7.3(m, 2H), 8.1(broad, 1H), 8.4(m, 2H). |
| 16 | [N-CH$_2$-C(OH)(CH$_2$OH)$_2$] | 3,4-dihydroxy isobutylene oxide | ‡1.7(m, 2H), 1.9(m, 2H), 2.3 (m, 2H), 2.5(m, 3H), 3.0(m, 2H), 3.5(AB q, 4H), 6.0(s, 1H), 6.9(m, 2H), 7.1(m, 2H), 7.3(m, 2H), 8.2(m, 2H). |
| 17* | [N-CH(CH$_3$)-CH(OH)-CH$_2$OH] racemic | Trans 4-hydroxy-2,3-epoxybutane | 1.0(d, J=6.8Hz, 3H), 1.7(m 2H), 2.0(m, 2H), 2.3(m, 1H), 2.6(m, 3H), 2.8(m, 2H), 3.0 (broad, 3H), 3.6(m, 3H), 6.1(s, 1H), 7.0(m, 2H), 7.2(m, 2H), 7.3(m, 2H), 8.2(m, 2H). |
| 18* | [N-CH(CH$_3$)-CH(OH)-CH$_2$OCH$_3$] racemic | Trans 4-methoxy-2,3-epoxybutane | 1.0(d, J=6.8Hz, 3H), 1.7(m 2H), 1.9(m, 2H), 2.3(m, 1H), 2.4(m, 1H), 2.5(m, 2H), 2.9 (m, 2H), 3.3(s, 3H), 3.4(m, 2H), 3.9(m, 1H), 6.1(s, 1H), 7.0(m, 2H), 7.2(m, 2H), 7.3 (m, 2H), 8.2(m, 2H). |

TABLE 1-continued

| Ex. | N—R | Epoxide | ¹H NMR (400 MHz, CDCl₃, ppm) |
|---|---|---|---|
| 19* | N with CH₃ and CH(OH)CH₂OH, racemic | Cis 4-hydroxy-2,3-epoxybutane | ‡1.0(d, J=6.6Hz, 3H), 1.7(m 2H), 2.0(m, 2H), 2.3(m, 2H), 2.7(m, 4H), 3.4(m, 2H), 3.8 (m, 1H), 6.1(s, 1H), 7.0(m, 2H), 7.2(m, 2H), 7.3(m, 2H), 8.3(m, 2H). |
| 20* | N with CH₃ and CH(OH)CH₂OCH₃, racemic | Cis 4-methoxy-2,3-epoxybutane | 1.0(d, J=6.7Hz, 3H), 1.8(m 2H), 2.0(m, 2H), 2.2(m, 1H), 2.7(m, 5H), 3.4(s, 3H), 3.5(m, 3H), 6.1(s, 1H), 7.0(m, 2H), 7.2(m, 2H), 7.3(m, 2H), 8.0 (broad, 1H), 8.4(m, 2H). |
| 21 | N with CH₃, CH(CH₃)CH(OH), racemic | Cis-2,3-epoxy-butane | 8.39(d, J=6.23Hz, 2H), 8.15(s, 1H), 7.29(m, 2H), 7.16(d, J=6.14Hz, 2H), 7.03(m, 2H), 6.18(s, 1H), 3.45(m, 1H), 2.87(m, 1H), 2.76(m, 1H), 2.73~2.57(m, 2H), 2.40(m, 1H), 2.25(m, 1H), 2.03(m, 2H), 1.88(m, 1H), 1.70(m, 1H), 1.16(d, J=5.95Hz, 2H), 0.94(d, J=6.67Hz, 2H). |
| 22 | N with CH₃, CH(CH₃)CH(OH), racemic | trans-2,3-epoxy-butane | 8.39(d, J=6.23Hz, 2H), 8.13(s, 1H), 7.39(m, 4H), 7.26(m, 3H), 7.03(m, 2H), 6.18(s, 1H), 3.45(m, 1H), 2.87(m, 1H), 2.76(m, 1H), 2.73~2.57(m, 2H), 2.40(m, 1H), 2.25(m, 1H), 2.03(m, 2H), 1.88(m, 1H), 1.70(m, 1H), 1.16(d, J=5.95Hz, 2H), 0.94(d, J=6.67Hz, 2H). |
| 23 | N with CH₃, CH(Ph)CH₂OH, racemic | 3-phenylglycidol | 8.37(d, J=6.15Hz, 2H), 8.15(s, 1H), 7.29(m, 2H), 7.16(d, J=6.14Hz, 2H), 7.13(d, J=6.22, 2H), 7.01(m, 2H), 6.10(d, J=2.64Hz, 1H), 4.40(m, 1H), 3.85~3.65(m, 3H), 3.10(m, 2H), 2.40(m, 2H), 2.05~1.65(m, 4H). |
| 24 | dimethylamino glycopyranose with OH, OH, OH, OAc | 1,2-anhydro-α-D-glycopyranose 3,4,6-triacetate | (in CD₃OD) 8.25(d, J=6.27Hz, 2H), 7.34(m, 2H), 7.25(d, J=6.31Hz, 2H), 7.09(m, 2H), 7.01(m, 2H), 6.17(s, 1H),). |

TABLE 1-continued

| Ex. | N—R | Epoxide | $^{1}$H NMR (400 MHz, CDCl$_3$, ppm) |
|---|---|---|---|
| 25 | (N-CH(CH(OH))-CH(C6H4-OCH3)-C(=O)OCH3) racemic | trans-methyl 3-(4-methoxy-phenyl)glycidate | 8.38(d, J=6.02Hz, 2H), 8.25(s, 1H), 7.26(m, 3H), 7.15(d, J=6.10Hz, 2H), 7.02(m, 2H), 6.85(m, 3H), 6.14(d, J=2.56Hz, 1H), 4.85(d, J=4.52Hz, 1H), 3.79(m, 4H), 3.69(m, 1H), 3.60(s, 3H), 3.32(m, 1H), 2.99(m, 1H), 2.58(m, 1H), 2.31(m, 1H), 2.03(m, 2H), 1.90(m, 2H), 1.79(m, 1H) |
| 26 | (N-CH(CH3)-CH(OH)-CH2CH3) | 2,3-epoxy-pentane | (in CD$_3$OD) 8.40(d, J=6.69Hz, 2H), 7.34(m, 2H), 7.76(d, J=6.69Hz, 2H), 7.47(m, 2H), 7.24(t, J=8.72, 2H), 6.59(d, J=2.40Hz, 1H), 3.63(m, 1H), 3.50(m, 2H), 3.40(m, 1H), 3.25(m, 2H), 3.03(m, 1H), 2.36(m, 2H), 2.25(m, 1H), 2.02(m, 1H), 1.75(m, 1H), 1.45(m, 1H), 1.33(d, J=6.78Hz, 3H), 1.05(t, J=7.38Hz, 3H); MS(ESI)=408.4 |
| 27 | (N-CH2-C(OH)(CH3)2 with extra CH3) | 2-methyl-propylene oxide | 8.38(d, 2H), 7.29(m, 2H), 7.16(d, 2H), 7.03(t, 2H), 6.18(d, 1H), 3.03(m, 2H), 2.60(m, 1H), 2.46(m, 2H), 1.95(m, 2H), 1.85(m, 2H), 2.37(s, 2H), 1.18(s, 6H) |
| 28 | (N-CH2-CH(OH)-CH2-O-CF2-CHF2) | 1,1,2,2-tetra-fluoroethyl glycidyl ether | 1.6(m, 4H), 1.8(m, 2H), 2.0 (m, 2H), 2.2(m, 1H), 2.5(m, 2H), 2.7(m, 1H), 3.0(m, 1H), 3.2(m, 1H), 3.4(m, 2H), 3.6 (m, 1H), 4.0(m, 1H), 5.7(t, J~50Hz, 1H), 6.2(s, 1H), 7.0 (m, 2H), 7.2(m, 2H), 7.3(m, 2H), 8.3(broad, 1H), 8.4(m, 2H) |
| 29 | (N-CH2-CH(OH)-CH2-O-CH(CH3)2) | isopropyl glycidyl ether | 1.2(d, J=6.1Hz, 6H), 1.9(m, 2H), 2.0(m, 2H), 2.2(m, 1H), 2.4(m, 1H), 2.5(m, 2H), 2.7 (m, 1H), 3.1(m, 1H), 3.2(m, 1H), 3.4(m, 2H), 3.6(m, 1H), 4.0(m, 1H), 6.2(s, 1H), 7.0(m, 2H), 7.2(m, 2H), 7.3(m, 2H), 8.3(broad, 1H), 8.4(m, 2H) |
| 30 | (N-CH2-CH(OH)-CH2-O-C(CH3)3) | tert-butyl glycidyl ether | 1.2(3, 9H), 2.0(m, 4H), 2.2(m, 1H), 2.4(m, 1H), 2.6(m, 2H), 2.7(m, 1H), 3.2(m, 2H), 3.4 (m, 2H), 3.9(m, 1H), 6.2(s, 1H), 7.0(m, 2H), 7.2(m, 2H), 7.3(m, 2H), 8.3(broad, 1H), 8.4(m, 2H) |

TABLE 1-continued

| Ex. | N—R | Epoxide | $^1$H NMR (400 MHz, CDCl$_3$, ppm) |
|---|---|---|---|
| 31 | N-CH$_2$-CH(OH)-CH$_2$-O-CH$_2$-(2-furyl) | furfuryl glycidyl ether | 1.8(m, 2H), 2.0(m, 2H), 2.2 (m, 1H), 2.5(m, 4H), 2.7(m, 1H), 3.0(m, 1H), 3.2(m, 2H), 3.5(m, 2H), 3.9(m, 1H), 4.5(s, 2H), 6.2(s, 1H), 6.3(m, 2H), 7.0(m, 2H), 7.2(m, 2H), 7.3 (m, 2H), 7.4(s, 1H), 8.3(broad, 1H), 8.4(m, 2H) |
| 32 | N-CH$_2$-CH(OH)-CH$_2$-S-(2-thienyl) | 2-thienyl thio-glycidyl ether | 1.8(m, 2H), 2.0(m, 2H), 2.2 (m, 1H), 2.3(m, 1H), 2.5(m, 2H), 2.6(m, 1H), 2.8(m, 2H), 3.0(m, 2H), 3.9(m, 1H), 6.1(s, 1H), 6.3(m, 2H), 7.0(m, 3H), 7.1(m, 3H), 7.3(m, 3H), 8.4 (m, 2H) |
| 33 | N-CH$_2$-C(CH$_3$)(OH)-CH=CH$_2$ | 2-vinyl-propylene oxide | 1.2(s, 3H), 1.8(m, 5H), 2.2(m, 1H), 2.4(AB, 2H), 2.6(m, 1H), 2.9(m, 1H), 3.1(m, 1H), 5.0 (dd, J=1.6, 10.6Hz, 2H), 5.3 (dd, J=1.6, 17.2Hz, 2H), 5.8 (dd, J=10.6, 17.2Hz, 2H), 6.2 (s, 1H), 7.0(m, 2H), 7.2(m, 2H), 7.3(m, 2H), 8.1(broad, 1H), 8.4(m, 2H) |
| 34 | N-CH$_2$-CH(OH)-CH$_2$-O-C$_6$H$_4$-NO$_2$ | 4-nitrophenyl glycidyl ether | 1.8(m, 2H), 2.0(m, 4H), 2.1 (m, 1H), 2.5(m, 1H), 2.6(m, 2H), 3.0(m, 1H), 3.2(m, 1H), 4.1(m, 2H), 6.2(s, 1H), 7.0(m, 4H), 7.2(m, 2H), 7.3(m, 2H), 8.2(m, 2H), 8.4(m, 2H) |
| 35 | N-CH$_2$-CH(OH)-CH$_2$-O-C$_6$H$_5$ | phenyl glycidyl ether | (+CD$_3$OD) 1.8(m, 2H), 2.0(m, 4H), 2.1(m, 1H), 2.4(m, 1H), 2.6(m, 2H), 3.0(m, 1H), 3.2 (m, 1H), 3.9(m, 1H) 4.1(m, 1H), 6.1(s, 1H), 6.9(m, 3H), 7.0(m, 2H), 7.2(m, 2H), 7.3 (m, 4H), 8.3(m, 2H) |
| 36 | N-CH$_2$-CH(OH)-CH$_2$-O-C$_6$H$_4$-OCH$_3$ | 4-methoxy-phenyl glycidyl ether | (+CD$_3$OD) 1.7(m, 2H), 1.9(m, 2H), 2.0(m, 1H), 2.2(m, 1H), 2.5(m, 3H), 3.0(m, 2H), 3.8 (m, 2H), 4.0(m, 1H), 6.0(s, 1H), 6.7(m, 4H), 6.9(m, 2H), 7.1(m, 2H), 7.2(m, 2H), 8.2 (m, 2H) |
| 37 | N-CH$_2$-CH(OH)-CH$_2$-O-C$_6$H$_4$-C(CH$_3$)$_3$ | 4-tert-butyl-phenyl glycidyl ether | (+CD$_3$OD) 1.2(s, 9H), 1.8(m, 2H), 1.9(m, 2H), 2.1(m, 1H), 2.3(m, 1H), 2.6(m, 3H), 3.1 (m, 2H), 3.9(m, 2H), 4.1(m, 1H), 6.1(s, 1H), 6.8(m, 2H), 7.0(m, 2H), 7.2(m, 2H), 7.3 (m, 4H), 8.2(m, 2H) |

TABLE 1-continued

| Ex. | N—R | Epoxide | ¹H NMR (400 MHz, CDCl₃, ppm) |
|---|---|---|---|
| 38 | N-CH₂-CH(OH)-CH₂-O-(4-chlorophenyl) | 4-chlorophenyl glycidyl ether | (+CD₃OD) 1.8(m, 2H), 1.9(m, 2H), 2.1(m, 1H), 2.3(m, 1H), 2.6(m, 3H), 3.0(m, 2H), 3.8 (m, 2H), 4.1(m, 1H), 6.1(s, 1H), 6.8(m, 2H), 7.0(m, 2H), 7.2(m, 4H), 7.3(m, 2H), 8.2 (m, 2H) |
| 39 | N-CH₂-CH(OH)-(CH₂)₆-CH=CH₂ | 1,2-epoxy-9-decene | (+CD₃OD) 1.3(m, 10H), 1.8 (m, 2H), 2.0(m, 3H), 2.2(m, 1H), 2.3(m, 2H), 2.4(m, 2H), 2.6(m, 1H), 3.0(m, 1H), 3.2 (m, 1H), 3.8(m, 1H), 4.9(m, 2H), 5.8(m, 1H), 6.1(s, 1H), 7.0(m, 2H), 7.2(m, 2H), 7.3 (m, 2H), 8.3(m, 2H) |
| 40 | N-CH₂-CH(OH)-(CH₂)₂-CH=CH₂ | 1,2-epoxy-5-hexene | (+CD₃OD) 1.4(m, 2H), 1.8(m, 2H), 2.0(m, 2H), 2.1(m, 2H), 2.2(m, 1H), 2.4(m, 3H), 2.6 (m, 1H), 3.0(m, 1H), 3.2(m, 1H), 3.8(m, 1H), 5.0(m, 2H), 5.8(m, 1H), 6.1(s, 1H), 7.0(m, 2H), 7.2(m, 2H), 7.3(m, 2H), 8.3(m, 2H) |
| 41 | N-CH₂-CH(OH)-(CH₂)₄-CH=CH₂ | 1,2-epoxy-7-octene | (+CD₃OD) 1.4(m, 6H), 1.8(m, 2H), 2.0(m, 4H), 2.1(m, 1H), 2.4(m, 2H), 2.6(m, 2H), 3.0 (m, 1H), 3.2(m, 1H), 3.8(m, 1H), 4.9(m, 2H), 5.8(m, 1H), 6.1(s, 1H), 7.0(m, 2H), 7.2(m, 2H), 7.3(m, 2H), 8.3(m, 2H) |
| 42 | N-CH₂-CH(OH)-(4-nitrophenyl) | 4-nitrostyrene oxide | (+CD₃OD) 1.8(m, 2H), 2.0(m, 2H), 2.2(m, 1H), 2.4(m, 1H), 2.5(m, 2H), 2.6(m, 1H), 2.9 (m, 1H), 3.2(m, 1H), 4.8(m, 1H), 6.1(s, 1H), 7.0(m, 2H), 7.2(m, 2H), 7.3(m, 2H), 7.5 (m, 2H), 8.2(m, 2H), 8.3(m, 2H) |
| 43 | N-CH₂-CH(OH)-(CH₂)₂-OAc | 5-acetoxy-1,2-epoxypentane | (+CD₃OD) 1.4(m, 2H), 1.7(m, 1H), 1.8(m, 3H), 2.0(m, 2H), 2.01(s, 3H), 2.1(m, 1H), 2.4 (m, 3H), 2.6(m, 1H), 3.0(m, 1H), 3.1(m, 1H), 3.8(m, 1H), 4.0(m, 2H), 6.1(s, 1H), 7.0(m, 2H), 7.2(m, 2H), 7.3(m, 2H), 8.3(m, 2H) |
| 44 | N-CH₂-CH(OH)-CH=CH₂ | 1,2-epoxy-3-butene | (+CD₃OD) 1.8(m, 2H), 2.0(m, 2H), 2.1(m, 1H), 2.4(m, 3H), 2.6(m, 1H), 3.0(m, 1H), 3.1 (m, 1H), 4.2(m, 1H), 5.1(d, J=10.4Hz, 1H), 5.3(d, J=17.2 Hz, 1H), 5.8(m, 1H), 6.1(s, 1H), 7.0(m, 2H), 7.2(m, 2H), 7.3(m, 2H), 8.3(m, 2H) |

TABLE 1-continued

| Ex. | N—R | Epoxide | ¹H NMR (400 MHz, CDCl₃, ppm) |
|---|---|---|---|
| 45 | (N-CH(CH=CH₂)-CH(OH)CH₃) | 1,2-epoxy-3-butene | (+CD₃OD) 1.8(m, 2H), 2.0(m, 2H), 2.2(m, 1H), 2.6(m, 2H), 2.9(m, 1H), 3.0(m, 1H), 3.1 (m, 1H), 3.6(m, 2H), 5.2(d, J=17.3Hz, 1H), 5.3(d, J=11.4 Hz, 1H), 5.8(m, 1H), 6.1(s, 1H), 7.0(m, 2H), 7.2(m, 2H), 7.3(m, 2H), 8.3(m, 2H) |
| 46 | (N-CH₂-CH(OH)-CH₂-O-(2-methylphenyl)) | 2-methylphenyl glycidyl ether | (in CD₃OD) 1.8(m, 2H), 2.0 (m, 2H), 2.1(m, 1H), 2.2(s, 3H), 2.4(m, 1H), 2.6(m, 3H), 3.0(m, 1H), 3.2(m, 1H), 3.9 (m, 2H), 4.2(m, 1H), 6.1(s, 1H), 6.8(m, 2H), 7.0(m, 2H), 7.1(m, 2H), 7.2(m, 2H), 7.3 (m, 2H), 8.3(m, 2H) |
| 47 | (N-CH₂-CH(OH)-O-CH(CH₃)(CH₂)₃CH₃) | 2-ethylhexyl glycidyl ether | 0.9(m, 6H), 1.3(m, 8H), 1.5 (m, 1H), 1.8(m, 2H), 2.0(m, 2H), 2.2(m, 1H), 2.4(m, 1H), 2.5(m, 2H), 2.6(m, 1H), 3.0 (m, 1H), 3.2(m, 1H), 3.3(m, 2H), 3.4(m, 2H), 4.0(m, 1H), 6.2(s, 1H), 7.0(m, 2H), 7.2(m, 2H), 7.3(m, 2H), 8.3(broad, 1H), 8.4(m, 2H) |
| 48 | (N-CH₂-CH(OH)-(CH₂)₃CH₃) | 1,2-epoxyhexane | (+CD₃OD) 0.8(t, J=7.0Hz, 3H), 1.3(m, 6H), 1.8(m, 2H), 2.0(m, 2H), 2.1(m, 1H), 2.4 (m, 3H), 2.6(m, 1H), 2.9(m, 1H), 3.1(m, 1H), 3.7(m, 1H), 6.1(s, 1H), 7.0(m, 2H), 7.2(m, 2H), 7.3(m, 2H), 8.3(m, 2H) |
| 49 | (N-CH₂-CH(OH)-(CH₂)₅CH₃) | 1,2-epoxyoctane | (+CD₃OD) 0.8(t, J=7.0Hz, 3H), 1.3(m, 10H), 1.8(m, 2H), 2.0(m, 2H), 2.1(m, 1H), 2.4 (m, 3H), 2.6(m, 1H), 3.0(m, 1H), 3.1(m, 1H), 3.7(m, 1H), 6.1(s, 1H), 7.0(m, 2H), 7.2(m, 2H), 7.3(m, 2H), 8.3(m, 2H) |
| 50 | (N-CH₂-CH(OH)-CH₂-O-(CH₂)₃CH₃) | butyl glycidyl ether | (+CD₃OD) 0.8(t, J=7.3Hz, 3H), 1.3(m, 2H), 1.5(m, 2H), 1.8(m, 2H), 1.9(m, 2H), 2.1 (m, 1H), 2.3(m, 1H), 2.5(m, 2H), 2.6(m, 1H), 3.1(m, 2H), 3.4(m, 4H), 3.9(m, 1H), 6.1(s, 1H), 7.0(m, 2H), 7.2(m, 2H), 7.3(m, 2H), 8.2(m, 2H) |
| 51 | (N-cyclohexyl with OH, racemic) | cyclohexene oxide | 1.2(m, 4H), 1.6(m, 4H), 1.8 (m, 2H), 2.0(m, 2H), 2.1(m, 1H), 2.4(m, 2H), 2.6(m, 1H), 2.8(m, 1H), 2.9(m, 1H), 3.0 (m, 1H), 3.4(m, 1H), 6.2(d, J=2.3Hz, 1H), 7.0(m, 2H), 7.2 (m, 2H), 7.3(m, 2H), 8.4(m, 2H) |

TABLE 1-continued

| Ex. | N—R | Epoxide | ¹H NMR (400 MHz, CDCl₃, ppm) |
|---|---|---|---|
| 52 | [N-CH₂-CH(OH)-CH₂-O-(4-fluorophenyl)] | 4-fluorophenyl glycidyl ether | (+CD₃OD) 1.8(m, 2H), 2.0(m, 2H), 2.1(m, 1H), 2.4(m, 1H), 2.6(m, 3H), 3.0(m, 1H), 3.1 (m, 1H), 3.9(d, J=5.1Hz, 2H), 4.1(m, 1H), 6.1(s, 1H), 6.8(m, 2H), 6.9(m, 2H), 7.0(m, 2H), 7.2(m, 2H), 7.3(m, 2H), 8.2 (m, 2H) |
| 53 | [N-CH₂-CH(R)(OH)-CH₂-O-benzyl] | (R)-benzyl glycidyl ether | 1.8(m, 2H), 2.0(m, 2H), 2.2 (m, 1H), 2.5(m, 3H), 2.6(m, 1H), 3.0(m, 1H), 3.2(m, 1H), 3.5(m, 2H), 4.0(m, 1H), 4.6(s, 2H), 6.2(s, 1H), 7.0(m, 2H), 7.2(m, 4H), 7.3(m, 7H), 8.2 (broad, 1H), 8.4(m, 2H) |
| 54 | [N-CH₂-CH(S)(OH)-CH₂-O-benzyl] | (S)-benzyl glycidyl ether | 1.8(m, 2H), 2.0(m, 2H), 2.2 (m, 1H), 2.5(m, 3H), 2.6(m, 1H), 3.0(m, 1H), 3.2(m, 1H), 3.5(m, 2H), 4.0(m, 1H), 4.6(s, 2H), 6.2(s, 1H), 7.0(m, 2H), 7.2(m, 4H), 7.3(m, 7H), 8.2 (broad, 1H), 8.4(m, 2H) |
| 55 | [N-CH₂-CH(OH)-CH₂-O-CH₂CH₂-O-CH₂-epoxide] | ethylene glycol bisglycidyl ether | 1.8(m, 2H), 2.0(m, 2H), 2.2 (m, 1H), 2.4(m, 3H), 2.6(m, 1H), 2.8(m, 1H), 3.0(m, 1H), 3.2(m, 2H), 3.4–4.0(m, 9H), 6.2(s, 1H), 7.0(m, 2H), 7.2(m, 4H), 7.3(m, 2H), 8.2(broad, 1H), 8.4(m, 2H) |
| 56 | [N-CH₂-CH(OH)-(CH₂)₄-epoxide] | 1,7-octadiene bisoxide | 1.5(m, 8H), 1.8(m, 2H), 2.0 (m, 2H), 2.2(m, 1H), 2.4(m, 4H), 2.7(m, 1H), 2.8(m, 1H), 3.0(m, 1H), 3.2(m, 2H), 3.9 (m, 1H), 6.2(s, 1H), 7.0(m, 2H), 7.2(m, 4H), 7.3(m, 2H), 8.2(broad, 1H), 8.4(m, 2H) |
| 57 | [N-CH₂-CH(OH)-CH₂-O-CH₂CH₂-O-CH₂-CH(OH)-CH₃] | ethylene glycol bisglycidyl ether | 1.8(m, 6H), 2.0(m, 4H), 2.2 (m, 2H), 2.5(m, 6H), 3.1(m, 4H), 3.4–4.0(m, 10H), 6.2(s, 2H), 7.0(m, 4H), 7.2(m, 4H), 7.3(m, 4H), 8.4(m, 4H) |
| 58 | [N-CH₂-CH(OH)-(CH₂)₄-CH(OH)-CH₃] | 1,7-octadiene bisoxide | 1.4(m, 8H), 1.8(m, 4H), 2.0 (m, 4H), 2.1(m, 2H), 2.4(m, 6H), 2.6(m, 2H), 2.9(m, 2H), 3.1(m, 2H), 3.7(m, 2H), 6.1(s, 2H), 7.0(m, 4H), 7.2(m, 4H), 7.3(m, 4H), 8.4(m, 4H) |
| 59 | [N-CH₂-CH(OH)-CH₂-CH₂-OH] | 4-hydroxy-1,2-epoxybutane | (+CD₃OD) 1.7(broad, 4H), 2.0 (m, 2H), 2.2–2.7(m, 5H), 3.0 (m, 2H), 3.8(m, 2H), 3.9(m, 1H), 6.2(s, 1H), 7.0(m, 2H), 7.2(m, 2H), 7.3(m, 2H), 8.4 (m, 2H). |

TABLE 1-continued

| Ex. | N—R | Epoxide | $^1$H NMR (400 MHz, CDCl$_3$, ppm) |
| --- | --- | --- | --- |
| 60 | (N with CH2-CH(OH)-CH2-CH(OH)-CH3) | 4-hydroxy-1,2-epoxypentane | (+CD$_3$OD) 1.2(m, 3H), 1.5–2.0 (m, 5H), 2.1–2.7(m, 6H), 3.0 (m, 2H), 4.0(m, 2H), 6.1(s, 1H), 7.0(m, 2H), 7.2(m, 2H), 7.3(m, 2H), 8.4(m, 2H). |
| 61 | (diastereomer A) | 4-hydroxy-3-methyl-1,2-epoxybutane | (+CD$_3$OD) 0.9(m, 3H), 1.6–2.0 (m, 5H), 2.1–2.7(m, 5H), 3.0 (m, 2H), 3.6(m, 2H), 3.7(m, 1H), 6.1(s, 1H), 7.0(m, 2H), 7.2(m, 2H), 7.3(m, 2H), 8.4 (m, 2H). |
| 62 | (diastereomer B) | 4-hydroxy-3-methyl-1,2-epoxybutane | (+CD$_3$OD) 0.9(m, 3H), 1.7–2.0 (m, 5H), 2.1(m, 1H), 2.3–2.7 (m, 4H), 3.1(m, 2H), 3.6(m, 2H), 3.8(m, 1H), 6.1(s, 1H), 7.0(m, 2H), 7.2(m, 2H), 7.3 (m, 2H), 8.4(m, 2H). |
| 63 | (N with CH2-CH(OH)-CH2-CH(OCH3)-CH2OH) | 4-hydroxy-3-methoxy-1,2-epoxybutane | 1.8(m, 3H), 2.0(m, 2H), 2.2–2.7(m, 4H), 3.1(m, 3H), 3.5 (2s, 3H), 3.7(m, 2H), 3.9(m, 2H), 6.2(s, 1H), 7.0(m, 2H), 7.2(m, 2H), 7.3(m, 2H), 8.2 (broad, 1H), 8.4(m, 2H). |
| 64 | (N with CH2-CH(OH)-CH2-CH(OCH3)-CH3) | 4-methoxy-1,2-pentane | 1.2(m, 3H), 1.6–2.2(m, 8H), 2.4(m, 2H), 2.7(m, 1H), 3.0 (m, 1H), 3.2(m, 1H), 3.4(2s, 3H), 3.8(m, 1H), 4.0(m, 1H), 6.2(d, J=2.9Hz, 1H), 7.0(m, 2H), 7.2(m, 2H), 7.3(m, 2H), 8.4(m, 2H). |
| 65 | (N-cyclopentane with OH, OH) | 3-hydroxycyclopentene oxide | 3.2(m, 2H), 3.2(m, 1H), 3.9 (m, 1H), 4.0(m, 1H), 4.1(m, 1H), 6.2(s, 1H) M+1: 422.2 |
| 66 | (N-cyclopentenone) | Cyclopentenone 2,3-oxide | 3.8(m, 2H), 6.2(d, 1H), 6.5(t, 1H) M+1: 402.2 |
| 67 | (N with CH2-CH(OH)-CH2-CH(OCO2CH3)-CH3) | 4-(methoxycarbonyloxy)-1,2-epoxypentane | 3.2(m, 1H), 3.3(m, 1H), 3.8(s, 3H), 4.0(m, 1H), 5.0(m, 1H), 6.2(d, 1H) M+1: 482.4 |

TABLE 1-continued

| Ex. | N—R | Epoxide | $^1$H NMR (400 MHz, CDCl$_3$, ppm) |
|---|---|---|---|
| 68 | (N with cyclopentane bearing two OH groups) | 4-hydroxycyclo-pentene oxide | (+CD$_3$OD) 3.1(m, 2H), 3.3(m, 1H), 4.2(m, 1H), 4.4(m, 1H), 6.2(s, 1H)<br>M+1: 422.1 |
| 69 | (N-CH$_2$-CH(OH)-CH$_2$-CH(OH)-CH$_3$, Syn) | Syn-4-hydroxy-1,2-epoxy-pentane | (+CD$_3$OD) 3.1(M, 1H), 3.2(m, 1H), 4.0(m, 2H), 6.2(s, 1H)<br>M+1: 424.4 |
| 70 | (N-CH(CH$_3$)-CH(OH)-CH$_3$, racemic) | cis-2,3-epoxy-butane | 8.39(d, J=6.23Hz, 2H), 8.15(s, 1H), 7.29(m, 2H), 7.16(d, J=6.14Hz, 2H), 7.03(m, 2H), 6.18(s, 1H), 3.45(m, 1H), 2.87(m, 1H), 2.76(m, 1H), 2.73~2.57(m, 2H), 2.40(m, 1H), 2.25(m, 1H), 2.03(m, 2H), 1.88(m, 1H), 1.70(m, 1H), 1.16(d, J=5.95Hz, 2H), 0.94(d, J=6.67Hz, 2H); MS(M+1)=394.3 |
| 71 | (N-CH(CH$_3$)-CH(OH)-CH$_3$, trans) | trans-2,3-epoxy butane | 8.39(d, J=6.23Hz, 2H), 8.13(s, 1H), 7.39(m, 4H), 7.26(m, 3H), 7.03(m, 2H), 6.18(s, 1H), 3.45(m, 1H), 2.87(m, 1H), 2.76(m, 1H), 2.73~2.57(m, 2H), 2.40(m, 1H), 2.25(m, 1H), 2.03(m, 2H), 1.88(m, 1H), 1.70(m, 1H), 1.16(d, J=5.95Hz, 2H), 0.94(d, J=6.67Hz, 2H); MS(M+1)=394.3 |
| 72 | (N-CH(R)(Ph)-CH(R)(OH)-CH$_3$) | (1R,2R)-(+)-1-phenylpropylene oxide | 7.30(m, 5H), 4.41(qn, J=5.85Hz, 1H), 3.14(d, J=5.09, 1H), 0.95(d, J=6.23Hz, 3H); MS(M+1)=456.3 |
| 73 | (N-CH(S)(Ph)-CH(S)(OH)-CH$_3$) | (1S,2S)-(−)-1-phenylpropylene oxide | 7.30(m, 5H), 4.41(qn, J=5.85Hz, 1H), 3.14(d, J=5.09, 1H), 0.95(d, J=6.23Hz, 3H); MS(M+1)=456.3 |
| 74 | (N-CH(CH$_2$OH)-CH(OH)-CH$_3$) | 2-methyl glycidol | 3.55~3.41(m, overlapping, 2H), 2.58(d, J=5.21Hz, 2H), 1.09(d, J=12.53Hz, 3H); MS(M+1)=410.3 |

TABLE 1-continued

| Ex. | N—R | Epoxide | $^1$H NMR (400 MHz, CDCl$_3$, ppm) |
|---|---|---|---|
| 75 | [structure with OH, OH, dioxole] | 2,2-dimethyl-5-oxiranyltetra-hydrofuro(2,3-D)(1,3)dioxol-6-ol | 5.94(d, J=3.67Hz, 1H), 4.47(d, J=3.58Hz, 1H), 4.28(d, J=2.57, 1H), 4.16(m, 1H), 4.06(m, 1H), 2.80(m, 1H), 2.57(m, 1H), 1.47(s, 3H), 1.29(s, 3H); MS(M+1)=524.5 |
| 76 | [structure with (S),(R), OH, OH, Ph] | (2S,3S)-(−)-3-phenylglycidol | 8.37(d, J=6.15Hz, 2H), 8.15(s, 1H), 7.29(m, 2H), 7.16(d, J=6.14Hz, 2H), 7.13(d, J=6.22, 2H), 7.01(m, 2H), 6.10(d, J=2.64Hz, 1H), 4.40(m, 1H), 3.85~3.65(m, 3H), 3.10(m, 2H), 2.40(m, 2H), 2.05~1.65(m, 4H); MS(M+1)=472.4 |
| 77 | [structure with (R),(S), OH, OH, Ph] | (2R,3R)-(+)-3-phenylglycidol | 7.36(m, 4H), 7.26(m, 1H), 4.40(m, 1H), 3.80(m, 1H), 3.70(m, 2H); MS(M+1)=472.4 |
| 78 | [structure with OH, OCH$_3$, OCH$_3$ phenyl] | methyl trans-3-(±)-(4-methoxy-phenyl)glycidate | 8.38(d, J=6.02Hz, 2H), 8.25(s, 1H), 7.26(m, 3H), 7.15(d, J=6.10Hz, 2H), 7.02(m, 2H), 6.85(m, 3H), 6.14(d, J=2.56Hz, 1H), 4.85(d, J=4.52Hz, 1H), 3.79(m, 4H), 3.69(m, 1H), 3.60(s, 3H), 3.32(m, 1H), 2.99(m, 1H), 2.58(m, 1H), 2.31(m, 1H), 2.03(m, 2H), 1.90(m, 2H), 1.79(m, 1H); MS(M+1)=530.4 |
| 79 | [structure with OH, ethyl] 2 HCl | 2,3-epoxy-pentane | (CD$_3$OD) 8.40(d, J=6.69Hz, 2H), 7.34(m, 2H), 7.76(d, J=6.69Hz, 2H), 7.47(m, 2H), 7.24(t, J=8.72, 2H), 6.59(d, J=2.40Hz, 1H), 3.63(m, 1H), 3.50(m, 2H), 3.40(m, 1H), 3.25(m, 2H), 3.03(m, 1H), 2.36(m, 2H), 2.25(m, 1H), 2.02(m, 1H), 1.75(m, 1H), 1.45(m, 1H), 1.33(d, J=6.78Hz, 3H), 1.05(t, J=7.38Hz, 3H); MS(M+1)=408.4 |
| 80 | [structure with OH, tetrahydrofuran] | 3,4-epoxytetra-hydrofuran | 4.40(m, 1H), 4.10(m, 1H), 3.98(m, 1H), 3.72(m, 1H), 3.68(m, 1H), 3.25(m, 1H); MS(M+1)=408.3 |
| 81 | [structure with OH, OCH$_3$, dioxole] | 2,2-dimethyl-5-oxiranyl-tetrahydro-furo(2,3-D)(1,3)dioxol-6-ol | 5.86(d, J=3.87Hz, 1H), 4.57(d, J=3.86Hz, 1H), 3.99(m, 1H), 3.92(m, 1H), 3.87(d, J=2.93Hz, 1H), 3.48(s, 3H), 2.74(m, 1H), 2.54(m, 1H), 1.47(s, 3H), 1.31(s, 3H); MS(M+1)=538.69 |

TABLE 1-continued

| Ex. | N—R | Epoxide | ¹H NMR (400 MHz, CDCl₃, ppm) |
|---|---|---|---|
| 82 | [N-CH₂-CH(OH)- attached to furanose-dioxolane-cyclohexane spiro system with OH] | [epoxide of furanose-dioxolane-cyclohexane spiro system] | 4.80(q, J=5.00Hz, 1H), 4.76(q, J=5.05Hz, 1H), 4.13(m, 1H), 4.03(m, 1H), 3.85(m, 1H), 3.83(m, 1H), 3.49(m, 1H), 3.44(m, 1H), 2.72(m, 1H), 2.42(m, 2H), 1.41(m, 6H) |
| 83 | [N-CH₂-CH(OH)-CH₂F] | 3-fluoro-1,2-epoxypropane | 1.62(s, 1H), 1.86(m, 2H); 4.02(m, 1H), 4.44(m, 2H). |
| 84 | [N-CH₂-C(OH)(CH₃)-C(O)OCH₃] | methyl 2,3-epoxy-2-methyl-acrylate | 1.86(s, 3H), 2.52(d, J=11.8Hz, 1H), 2.96(d, J=11.8Hz, 1H), 3.78(s, 3H). |
| 85 | [N-CH₂-CH(OH)(R)-CH₂-OC(O)n-C₃H₇] | (R)-glycidyl butyrate | 0.95(t, J=7.6Hz, 3H), 1.66(m, 2H), 2.34(t, J=7.8Hz, 2H), 2.96(m, 2H), 3.82(m, 1H), 4.02(bs, 1H), 4.10(m, 2H). |
| 86 | [N-CH(R)(CO₂CH₂CH₃)-CH(S)(OH)(CH₃)] | ethyl (2S,3S)-2,3-epoxy-3-methyl-propanoate | 1.18(d, J=6.0Hz, 3H), 1.28(t, J=7.1Hz, 3H), 2.91(d, J=9.9Hz, 1H), 3.92(m, 1H), 4.22(m, 2H). |
| 87 | [N-attached to 3-hydroxy tetrahydrothiophene-1,1-dioxide] | 3,4-epoxy tetrahydrothiophene-1,1-dioxide | 2.26(m, 1H), 2.38(m, 1H), 2.58(m, 1H), 3.05(m, 1H), 3.48(m, 1H), 4.46(m, 1H). |
| 88 | [N-CH(R)(CH₃)-CH(S)(OH)(CO₂CH₂CH₃)] | ethyl (2S,3S)-2,3-epoxy-3-methyl-propanoate | 1.09(m, 3H), 1.30(m, 3H), 2.90(m, 1H), 3.92(m, 1H), 4.24(m, 2H). |
| 89 | [N-CH(S)(CH₃)-CH(R)(OH)(CO₂CH₂CH₃)] | ethyl (2R,3R)-2,3-epoxy-3-methyl-propanoate | 1.18(d, J=6.0Hz, 3H), 1.28(t, J=7.1Hz, 3H), 2.91(d, J=9.9Hz, 1H), 3.92(m, 1H), 4.22(m, 2H). |

TABLE 1-continued

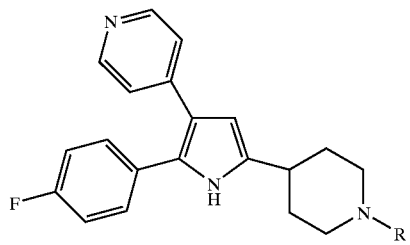

| Ex. | N—R | Epoxide | $^1$H NMR (400 MHz, CDCl$_3$, ppm) |
|---|---|---|---|
| 90 | N(S)—(R) with OH and CO$_2$CH$_2$CH$_3$ | ethyl (2R,3R)-2,3-epoxy-3-methyl-propanoate | 1.09(m, 3H), 1.30(m, 3H), 2.88(m, 1H), 3.92(m, 1H), 4.24(m, 2H). |
| 91 | N–CH$_2$–CH(OH)–CH$_2$–O–CH$_2$CN | glycidyl cyanomethyl ether | 2.52(m, 2H), 3.52(m, 2H), 3.96(m, 1H), 4.28(d, J=3.5Hz, 2H). |
| 92 | N–CH$_2$–(R)CH(OH)–(3-Cl-C$_6$H$_4$) | 3-chloro-(R)-styrene epoxide | 2.52(m, 2H), 4.75(m, 1H), 7.24(m, 2H), 7.38(s, 1H). |
| 93 | N–CH$_2$–C(OH)(CH$_3$)–C$_6$H$_5$ | 1,2-epoxy-2-phenylpropane | 1.48(s, 3H), 2.70(d, J=9.6Hz, 1H), 2.78(d, J=9.4Hz, 1H), 7.24(m, 5H). |
| 94 | N–CH$_2$–CH(OH)–CCl$_3$ | 3,3,3-trichloro propylene oxide | 2.72(m, 1H), 2.95(dd, J=12.8, 4.2Hz, 1H), 4.27(dd, J=9.4, 4.0Hz, 1H). |
| 95 | N–CH$_2$–CH(OH)–C(CH$_3$)$_3$ | 3,3-dimethyl-1,2-epoxybutane | 0.94(s, 9H), 2.38(m, 2H), 3.39(m, 1H). |
| 96 | N–CH$_2$–CH(OH)–(CH$_2$)$_2$–OAc | 5-acetyloxy-1,2-epoxypentane | 1.45(m, 2H), 1.82(m, 4H), 2.10(s, 3H), 3.72(m, 1H), 4.08(m, 2H). |
| 97 | N–CH$_2$–CH(OH)–CH$_2$–P(O)(OCH$_2$CH$_3$)$_2$ | diethyl 2,3-epoxypropyl-phosphonate | 1.30(m, 6H), 1.98(m, 2H), 2.40(m, 2H), 4.06(m, 4H), 4.18(m, 1H). |
| 98 | N–CH$_2$–CH(OH)–CH$_2$–C(OH)(CH$_3$)$_2$ | 1,2-epoxy-4-hydroxy-4-methylpentane | 1.18(s, 3H), 1.30(s, 3H), 1.54(m, 2H), 2.36(m, 2H), 4.11(m, 1H). |

TABLE 1-continued

| Ex. | N—R | Epoxide | ¹H NMR (400 MHz, CDCl₃, ppm) |
| --- | --- | --- | --- |
| 99 | N—CH₂—CH(OH)—CH₂—C(CH₃)₂—OCH₃ | 1,2-epoxy-4-methoxy-4-methylpentane | 1.24(m, 6H), 1.54(m, 2H), 2.34(m, 2H), 3.21(s, 3H), 4.02(m, 1H). |
| 100* | N—CH(CH₃)—CH(OH)—CH(OH)—CH₂CH₃ | 2,3-epoxy-4-hydroxyhexane | 1.00(t, J=7.4Hz, 3H), 1.09(d, J=6.8Hz, 3H0, 1.62(m, 2H), 2.80(m, 1H), 3.56(m, 1H), 3.65(m, 1H). |
| 101 | N—CH₂—CH(OH)—CH₂—CH(OH)—CH₂CH₃ | 1,2-epoxy-4-hydroxyhexane | 0.92(m, 3H), 1.56(m, 2H), 1.80(m, 2H), 2.14(m, 1H), 2.44(m, 1H), 2.98(m, 1H), 3.80(m, 1H). |
| 102 | N—CH₂—CH(OH)—CH₂—CH(OCH₃)—CH₂CH₃ | 1,2-epoxy-4-methoxyhexane | 0.88(m, 3H), 1.56(m, 2H), 1.76(m, 1H), 2.58(m, 1H), 2.36(m, 2H), 3.45(m, 1H), 3.89(m, 1H). |
| 103* | N—CH(CH₃)—CH(OH)—CH(OH)—CH₃ | 2,3-epoxy-4-hydroxypentane | 1.08(d, J=6.7Hz, 3H), 1.19(d, J=6.4Hz, 3H), 2.80(m, 1H), 3.56(m, 1H), 3.95(m, 1H). |
| 104* | N—CH(CH₃)—CH(OH)—CH(OCH₃)—CH₂CH₃ | 2,3-epoxy-4-methoxyhexane | 0.92(t, J=6.0Hz, 3H), 1.09(d, J=5.6Hz, 3H), 1.56(m, 2H), 2.62(m, 1H), 3.38(m, 1H), 3.42(s, 3H), 3.48(m, 1H). |
| 105* | N—CH(CH₃)—CH(OH)—CH(OCH₃)—CH₃ | 2,3-epoxy-4-methoxypentane | 1.06(d, J=6.8Hz, 3H), 1.15(d, J=6.1Hz, 3H), 2.64(m, 1H), 3.36(s, 3H), 3.46(m, 2H). |
| 106 | N—CH₂—CH(OH)—CH(CH₃)—CH₂—CH₂OH | 1,2-epoxy-3-methyl-5-hydroxypentane | 0.90(d, J=6.7Hz, 3H), 1.79(m, 3H), 2.50(m, 2H), 3.49(m, 1H), 3.64(m, 1H), 3.74(m, 1H). |
| 107 | N—CH₂—CH(OH)—CH₂—C(OH)(CH₃)(Ph) | 1,2-epoxy-4-hydroxy-4-phenylpentane | 1.43(s, 3H), 1.82(m, 2H), 2.62(m, 2H), 3.82(m, 1H), 7.30(m, 5H). |

TABLE 1-continued

| Ex. | N—R | Epoxide | ¹H NMR (400 MHz, CDCl₃, ppm) |
|---|---|---|---|
| 108 | (N-CH₂-CH(OH)-CH₂-C(OCH₃)(CH₃)(Ph)) | 1,2-epoxy-4-methoxy-4-phenylpentane | 1.4(s, 3H), 1.76(m, 2H), 3.21(s, 3H), 3.92(m, 3H), 7.42(m, 5H). |
| 109 | (N-CH₂-CH(OH)-CH₂-CH(OH)-C(CH₃)₃) | 1,2-epoxy-4-hydroxy-5,5-dimethylhexane | 0.93(s, 9H), 2.06(m, 2H), 2.51(m, 2H), 3.52(m, 1H), 4.04(m, 1H). |
| 110 | (N-CH₂-CH(OH)-CH₂-CH(OH)-C(CH₃)₃) | 1,2-epoxy-4-hydroxy-5,5-dimethylhexane | 0.93(s, 9H), 1.60(m, 2H), 2.52(m, 2H), 3.60(m, 1H), 4.08(m, 1). |
| 111* | (N-CH(CH₃)-CH(OH)-CH(OH)-CH(CH₃)₂) | 2,3-epoxy-4-hydroxy-5-methylhexane | 0.98(d, J=6.6Hz, 3H), 1.04(d, J=6.4Hz, 3H), 1.14(d, J=6.4Hz, 3H), 1.80(m, 1H), 2.80(m, 1H), 3.48(m, 1H), 3.61(m, 1H). |
| 112 | (N-CH₂-CH(OH)-CH(OH)-CH(CH₃)₂) | 1,2-epoxy-4-hydroxy-5-methylhexane | 0.96(m, 6H), 1.91(m, 2H), 1.76(m, 1H), 2.20(m, 1H), 2.52(m, 1H), 3.62(m, 1H), 4.02(m, 1H). |

*Acetonitrile was used as solvent and 10 eq of LiClO4 was used as catalyst. The reaction was carried out at room temperature for 3 days.
‡in CDCl₃ + CD₃OD The following compounds were prepared by dissolving the corresponding acetonide precursor in aqueous hydrochloric acid 2N, 10 ml) and refluxing the solution for 3 hours. After evaporation the residue was decolorized with charcoal by refluxing in methanol. The mixture was filtered and evaporated to yield the desired product.

| Ex. | N–R | Acetonide NMR |
|---|---|---|
| 113 (2HCl) | (N-CH₂-CH(OH)-CH(tetrahydrofuran-2,3,4-triol)) | Ex. 75 (CD₃OD)8.40(d, J=6.83Hz, 2H), 7.76(d, J=7.01Hz, 2H), 7.47(m, 2H), 7.23(m, 2H), 6.59(s, 1H); MS(M+1)=484.3 |

| Ex. | N–R | Acetonide | NMR |
|---|---|---|---|
| 114 | 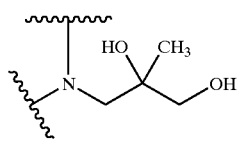 | Ex. 81 | (CD₃OD)4.48(d, J=7.74Hz, 1H), 4.05(m, 1H), 3.63(s, 3H), 3.50(m, 1H), 3.39(m, 1H), 3.2(m, 1H), 3.10(m, 1H), 2.60(m, 1H) |

EXAMPLE 115

To a stirred suspension of the compound of Example 84 (60 mg, 0.137 mmol) in 2.5 mL THF was added lithium aluminum hydride (1.0M in THF, 0.27 mL, 0.27 mmol) dropwise. After refluxing for 1 hour, the reaction was quenched with drops of saturated Na₂SO₄, and then solvent was removed in vacuo. Purification by silica gel chromatography eluting with 6–7% methanol (10% NH4OH) in dichloromethane afforded the desired compound (50 mg, 89%). NMR 1.08(s, 3H), 2.58(m, 2H), 3.47(d, J=11.1 Hz, 1H), 3.66(d, J=11.1 Hz, 1H), 3.67(m, 1H)

The following compounds were prepared by following the general procedure of Example 115

EXAMPLE 120

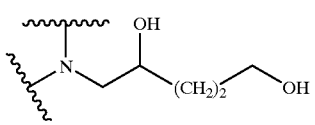

To a stirred solution of the compound of Example 96 (82 mg, 0.176 mmol) in 1 mL methanol was added 2N HCl/MeOH (0.35 mL, 0.704 mmol). After stirring for 24 hours, solvent was evaporated to yield the dihydrochloride salt of the title compound (93 mg). NMR 1.62(m, 4H), 3.14(m, 2H), 3.62(m, 2H), 4.08(m, 1H).

EXAMPLE 121

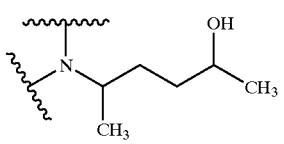

| Ex. | N–R | Starting Material | NMR |
|---|---|---|---|
| 116 | | Ex. 86 | 1.19(d, J=6.2Hz, 3H), 2.9(m, 1H), 3.69(m, 3H). |
| 117 | | Ex. 88 | 1.03(d, J=6.7Hz, 3H), 2.65(m, 1H), 3.45(m, 1H), 3.54(dd, J=4.3, 11.7Hz, 1H), 3.74(dd, J=2.9, 11.7Hz, 1H). |
| 118 | | Ex. 90 | 1.03(b, J=6.7Hz, 3H), 2.65(m, 1H), 3.45(m, 1H), 3.54(m, 1H), 3.70(m, 1H). |
| 119 | | Ex. 89 | 1.20(d, J=6.0Hz, 3H), 2.9(m, 1H), 3.69(m, 3H). |

The compound of reference example (50 mg, 0.156 mmol) and 2,5-hexanedione (27 mg, 0.234 mmol) were dissolved in ethanol (3 ml). Borane-pyridine complex(29 ul, 0.234 mmol) was added and the reaction mixture was heated at 60° C. overnight. The reaction mixture was concentrated and purified by prep-TLC eluting with 5%MeOH (10%NH3.H2O)/CH2Cl2 to give the desired compound in 40% yield. The temperature of the reactions could be from room temperature to 60° C. NMR 1.0(d, J=6.8 Hz, 3H), 1.1(d, J=6.2 Hz, 3H), 1.4(m, 1H), 1.5(m, 1H), 1.6(m, 1H), 1.8(m, 1H), 1.9(br, 4H), 2.2(m, 1H), 2.7(br, 3H), 2.8(m, 1H), 3.0(m, 1H), 3.7(m, 1H), 6.1(d, J=2.8 Hz, 1H), 7.0(m, 2H), 7.1(m, 2H), 7.3(m, 2H), 8.4(m, 2H), 9.6(br, 1H)

The following compounds were prepared according to the general procedure described in Example 121:

| Ex. | N–R | Carbonyl | $^1$H NMR (400 MHz, CDCl$_3$, ppm): |
|---|---|---|---|
| 122 | N(CH₂)₃—OH, CH₃ | 5-hydroxy-2-pentanone | 1.1(d, J=6Hz, 3H), 1.7(m, 4H), 2.0(m, 4H), 2.4(m, 1H), 2.8(m, 3H), 3.0(m, 2H), 3.6(m, 2H), 6.1(s, 1H), 7.0(m, 2H), 7.2(m, 2H), 7.4(m, 2H), 8.4(m, 2H), 9.7(broad, 1H). |
| 123 | N(CH₂)₃OH | glutaric dialdehyde | 1.4(m, 2H), 1.6(m, 4H), 1.9(m, 4H), 2.1(m, 2H), 2.4(t, J=7.0Hz, 2H), 2.6(m, 1H), 3.0(broad, 1H), 3.1(m, 2H), 3.6(t, J=6.2Hz, 3H), 6.1(d, J=2.8Hz, 1H), 7.0(m, 2H), 7.1(m, 2H), 7.3(m, 2H), 8.4(m, 2H), 9.2(broad, 1H). |
| 124 | (dihydrofuran with 2,2-dimethyl) | 1,2-dihydro-2,2-(dimethyl)furanone | (+CD₃OD)1.4(s, 6H), 2.0(m, 5H), 2.9(m, 1H), 3.6(m, 4H), 5.2(d, J=12.5Hz, 1H), 6.2(s, 1H), 7.0(m, 2H), 7.2(m, 2H), 7.3(m, 2H), 7.7(d, J=12.5Hz, 1H), 8.4(m, 2H) |
| 125 | N–CH(CH₃)–CH₂–CH₂–O–CH₂Ph | 4-benzyloxy-2-butanone | 1.1(d, J=6.6Hz, 3H), 1.6(m, 1H), 1.8(m, 2H), 2.0(m, 3H), 2.4(m, 1H), 2.5(m, 1H), 2.6(m, 1H), 3.0(m, 2H), 3.6(m, 2H), 4.5(s, 2H), 6.2(s, 1H), 6.5(s, 1H), 7.0(m, 2H), 7.2(m, 2H), 7.3(m, 7H), 8.4(m, 2H), 8.6(broad, 1H) |
| 126 | N–CH(CH₂OCH₃)₂ | 1,3-dimethoxy acetone | 1.8(m, 2H), 2.0(m, 2H), 2.6(m, 3H), 2.9(m, 1H), 3.1(m, 2H), 3.4(s, 6H), 3.6(m, 4H), 6.2(s, 1H), 7.0(m, 2H), 7.2(m, 2H), 7.3(m, 2H), 8.3(broad, 1H), 8.4(m, 2H) |
| 127 | N–CH(CH₂OCH₂Ph)(CH₂OCH₃) | 1-methoxy-3-benzyloxyacetone | 1.8(m, 2H), 2.0(m, 2H), 2.6(m, 3H), 2.9(m, 1H), 3.1(m, 2H), 3.4(s, 3H), 3.5–3.7(m, 4H), 4.6(s, 2H), 6.2(d, 1H), 7.0(m, 2H), 7.3(m, 9H), 8.4(m, 2H) |
| 128 | N–CH₂CH₂–OCH₂Ph | 2-benzyloxyacetaldehyde | 2.68(t, J=6.5Hz, 2H), 3.64(t, J=5.8Hz, 2H), 4.56(s, 2H), 7.36(m, 5H). |
| 129 | N–CH₂CH₂CH₂–SCH₃ | 3-(methylthio)-propionaldehyde | 1.74(m, 2H), 2.02(m, 2H), 2.12(s, 3H), 2.50(m, 2H). |
| 130 | N–CH(CH₃)CH₂CH₂SCH₃ | 4-methylthio-2-butanone | 1.02(d, J=6.6Hz, 3H), 1.54(m, 2H), 2.10(s, 3H), 2.56(m, 2H), 2.82(m, 1H). |

| Ex. | N–R | Carbonyl | $^1$H NMR (400 MHz, CDCl$_3$, ppm): |
|---|---|---|---|
| 131 | (N-methyl, CH(CH3)CH2CH2CH(OH)CH3) | 2,5-hexanedione | 0.98(d, J=6.8Hz, 3H), 1.15(d, J=6.2Hz, 3H), 1.93(m, 4H), 2.66(m, 1H), 3.71(m, 1H). |
| 132 | (N-methyl, 2,2-dimethyl-1,3-dioxan-5-yl) | 2,2-dimethyl-1,3-dioxane-5-one | 1.39(s, 3H), 1.40(s, 3H), 2.64(m, 1H), 3.86(m, 2H), 4.02(m, 2H). |
| 133 | (N-methyl, (CH2)4OH) | 2-hydroxy-terahydrofuran | 1.68(m, 4H), 2.11(m, 2H), 3.55(m, 2H). |
| 134 | (N-methyl, CH(CH3)CH2CH2OCH3) | 4-methoxy-2-butanone | 1.02(d, J=6.7Hz, 3H), 1.52(m, 1H), 1.86(m, 1H), 2.78(, 1H), 3.42(m, 2H), 3.32(s, 3H). |
| 135 | (N, CH(CH3)CH2CH(OCH3)2) | Acetyl acetaldehyde | 4.52(m, 1H), 3.33(s, 3H), 3.31(s, 3H), 2.82(m, 1H), 2.80(m, overlapping, 1H), 1.53(m, 1H), 1.01(d, J=6.67Hz, 3H); MS(M+1)=438.1 |
| 136 | (N, CH(CH3)CH2OPh) | Phenoxy-2-propanone | 7.27(m, overlapping, 2H), 7.92(m, 3H), 4.07(m, 1H), 3.89(m, 1H), 3.03(m, overlapping, 1H), 1.19(d, J=6.72Hz, 3H); MS(M+1)=456.3 |
| 137 | (N, CH2-cyclopropyl-CO2CH2CH3) | Ethyl 2-formyl-1-cyclopropane-carboxylate | 4.11(q, J=7.16Hz, 2H), 2.50~2.30(m, 2H), 1.75(m, 1H), 1.55(m, 1H), 1.42(m, 1H), 1.24(t, J=7.08Hz, 3H), 0.76(m, 1H); MS(M+1)=448.4 |
| 138 | (N, CH2-C(R)(OH)-C(S)(OH)-CH2OH) | D-erythrose | (CD$_3$OD) 3.75(m, 2H), 3.60(m, 2H), 2.73(m, 1H), 2.53(m, 1H); MS(M+1)=426.3 |
| 139 | (N, CH2-C(R)(OH)-C(S)(OH)-CH2OH) | L-(+)-erythrose | (CD$_3$OD) 3.79(q, J=6.23Hz, 1H), 3.72(m, 1H), 3.60(m, 2H), 2.73(m, 1H), 2.53(m, 1H); MS(M+1)=426.3 |
| 140 | (N, CH2-CH(OH)-CH(OH)-CH(OH)-CH(OH)-CH2OH) | d-mannitol | 1.82–4.0(m, 17H), 6.2(s, Pyrole) 7.08–7.11(t, J=8.7 2H F—Ar), 7.24–7.26(m, 2H Pyr) 7.33–7.37(m, 2H F—Ar), 8.25–8.26(m, 2H Pyrd) |

-continued

| Ex. | N–R | Carbonyl | $^1$H NMR (400 MHz, CDCl$_3$, ppm): |
|---|---|---|---|
| 141 | ![structure with N, HO, OH, OH, HO substituents] | 1-fucose | 1.25(d, J=6.6Hz CH$_3$), 1.80–1.90(m, 2H), 2.04–2.07(m, 2H), 2.38–2.489(m, 2H), 2.68–2.82(m, 3H), 3.19–3.28(m, 2H), 3.41–3.56(m, 2H)4.03—4.13(m, 2H) 6.20(s, Pyrrole), 7.01(t, J=9.0 2H F—Ar), 7.25(d, J=6.2Hz Pyr), 7.33–7.36(m, 2H F—Ar), 8.25(d,J=6.2Hz Pyr) |
| 142 | ![structure with N, OH, OH, HO, HO substituents] | 1-rhamnose | 1.28(d, J=6.4Hz CH$_3$), 1.79–1.81(m, 2H), 2.02–2.05(m, 2H), 2.31–2.38(m 2H), 2.54–3.25(m, 5H), 3.425(d, J=7.8Hz), 3.78–3.88(m, 4H), 6.20(s, Pyrrole), 7.10(t, J=8.7 2H F—Ar), 7.25(d, J=6.2Hz Pyr), 7.33–7.36(m, 2H F—Ar), 8.25(d, J=6.2Hz Pyr) |

EXAMPLE 143

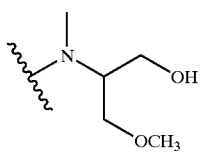

The compound of Example 127 (100 mg) was dissolved in methanol (10 mL) and Pd(OH)$_2$ on carbon (approx. 20 mg) and formic acid (5 drops) were added. The reaction mixture was shaken under hydrogen (approx. 45 lb) for 3 days, filtered and washed with 10% methanol in dichloromethane. Purification of the crude product by preparative TLC (silica, ammonium hydroxide/methanol/dichloromethane 0.5:6:93) yielded the title compound (10.3 mg). M+1: 410.2

EXAMPLES 144 AND 145

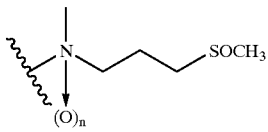

Ex. 144: n = 0
Ex. 145: n = 1

To a stirred mixture of the compound of Example 129 (76 mg, 0.186 mmol) in 3 mL CH$_2$Cl$_2$ at 0° C. was added m-chloroperoxybenzoic acid (56 mg, 70%, 0.227 mmol). After stirring for 2.5 hours, the reaction was quenched with a solid of K2CO3 and then stirred overnight. The mixture was filtrated and washed with CH2Cl2, then solvent was removed in vacuo. Purification by preparative TLC eluting with 11% methanol (containing 10% NH4OH) in dichloromethane afforded compound of Example 144 (23 mg) and compound of Example 145 (30 mg).

NMR

Example 144: 1.72(m 2H), 2.54(s, 3H), 2.55(m, 2H), 2.76(m, 2H).

Example 145: 1.98(m, 2H), 2.46(m, 2H), 2.54(s, 3H), 2.78(m, 2H).

EXAMPLE 146

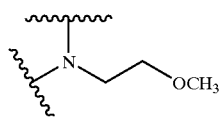

To a solution of the piperidine prepared in reference example (160 mg, 0.50 mmol) in anhydrous N,N-dimethylformamide (20 ml) under nitrogen at room temperature, sodium hydride (22 mg, 0.55 mmol, 60% dispersion in mineral oil) was added. The solution was stirred at room temperature for 0.5 hour and 2-bromo ethyl methyl ether (0.052 ml, 0.55 mmol) was added. The resulting solution was stirred at room temperature overnight. The crude product was quenched with water and extracted with ethyl acetate. The organic phase was concentrated and purified by flash column silica gel chromatography (MeOH—CH$_2$Cl$_2$, 10:90 v/v containing 1% NH$_4$OH, yield 41 mg of the title product. NMR (CDCl$_3$) δ8.38(d, J=6.10 Hz, 2H), 8.15(s, 1H), 7.15(d, J=6.14 Hz, 2H), 7.02(t, J=8.68 Hz, 2H), 6.16(d, J=2.85 Hz, 1H), 3.58(t, J=6.06 Hz, 2H), 3.49(qt, J=7.00 Hz, 2H), 3.07(d, J=11.35 Hz, 2H), 2.62(m, 3H), 2.15(t, J=10.99 Hz, 2H), 1.97(d, J=12.17 Hz, 2H), 1.84(m, 2H), 1.19(t, J=7.00 Hz, 3H); MS(CI)=380.2

EXAMPLE 147

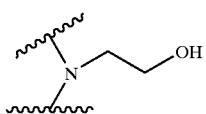

A mixture of the compound of reference example (80 mg), 0.3 mL DMF, 11 mg 40% NaH in mineral oil was stirred at room temperature for 30 minutes and to that 20 uL of 2-iodoethanol was added and heated at 90 degrees for 4 hours. Purification of the new more mobile spot by preparative TLC (Silica, ammonium hydroxide/methanol/dichloromethane 1:9:90) gave 66.1 mg of the desired compound. NMR (CDCl$_3$) characteristic peaks δ3.62(t, 2H), 3.0(d, 2H), 2.62(m, 1H), 2.58(t, 2H), 2.18(m, 2H), 2.02(d, 2H), 1.8(m, 2H).

The following compounds were prepared according to the general procedure described in Examples 146 and 147:

| Ex. | N—R | Alkyl halide | NMR (CDCl$_3$) |
| --- | --- | --- | --- |
| 148 | | (S)-3-bromo-2-methylpropanol | 8.38(d, J=6.23Hz, 2H), 8.17(s, 1H), 7.27(m, 2H), 7.15(d, J=6.18Hz, 2H), 7.02(m, 2H), 6.15(d, J=2.93Hz, 1H), 3.65(m, 1H), 3.49(t, J=10.41Hz, 1H), 3.33(d, J=10.42Hz, 1H), 2.97(d, J=11.80Hz, 1H), 2.63(m, 1H), 2.45(m, 2H), 2.25(m, 1H), 2.16(m, 1H), 2.05~1.90(m, 3H), 1.75(m, 2H), 0.73(d, J=6.75Hz, 3H); MS(ESI)=394.3 |
| 149 | | (R)-3-bromo-2-methylpropanol | 8.38(d, J=6.18Hz, 2H), 8.20(s, 1H), 7.27(m, 2H), 7.15(d, J=6.19Hz, 2H), 7.02(m, 2H), 6.15(d, J=2.85Hz, 1H), 3.65(m, 1H), 3.48(t, J=10.34Hz, 1H), 3.32(m, 1H), 2.97(d, J=11.35Hz, 1H), 2.63(m, 1H), 2.45(m, 2H), 2.25(m, 1H), 2.16(m, 1H), 2.05~1.90(m, 3H), 1.75(m, 2H), 0.73(d, J=6.83Hz, 3H); |
| 150 | | Epichlorohydrin | 3.16(m, 1H), 2.88(m, 1H), 2.79(t, J=4.35Hz, 1H), 2.50(m, 1H), 2.30(m, 1H) |
| 151 | | 2-bromomethyl-1,3-dioxolane | 5.06(t, J=4.51Hz, 1H), 3.97(m, 2H), 3.85(m, 2H), 2.66(d, J=4.44Hz, 2H) |
| 152 | | 2-chloroethyl-methyl sulfide | 2.63(m, overlapping, 4H), 2.13(s, 3H) |
| 153 | | 3-bromopropionaldehyde dimethyl acetal | 4.45(t, J=5.69Hz, 1H), 3.32(s, 6H), 1.80(m, 4H) |
| 154 | | Tetrahydrofurfuryl bromide | 4.07(qn, J=3.74Hz, 1H), 3.85(m, 1H), 3.74(m, 1H), 2.52(d, J=5.86Hz, 2H), 1.87(m, overlapping, 4H) |
| 155 | | 1-bromo-2-(2-methoxyethoxy)ethane | 3.63(m, 4H), 3.54(m, 2H), 3.36(s, 3H), 2.63(t, J=6.02Hz, 2H) |
| 156 | | 4-(chloromethyl)-2,2-dimethyl-1,3-dioxolane | 4.28(qn, J=5.42Hz, 1H), 4.06(m, 1H), 3.59(t, J=7.77Hz, 1H), 2.58(m, 1H), 2.47(m, 1H), 1.40(s, 3H), 1.35(s, 3H) |

-continued

| Ex. | N—R | Alkyl halide | NMR (CDCl$_3$) |
|---|---|---|---|
| 157 | ~N(CH$_2$CH$_2$OCH$_2$CH$_3$)~ | 2-bromoethyl ethyl ether | 8.38(d, J=6.10Hz, 2H), 8.15(s, 1H), 7.15(d, J=6.14Hz, 2H), 7.02(t, J=8.68Hz, 2H), 6.16(d, J=2.85Hz, 1H), 3.58(t, J=6.06Hz, 2H), 3.49(qt, J=7.00Hz, 2H), 3.07(d, J=11.35Hz, 2H), 2.62(m, 3H), 2.15(t, J=10.99Hz, 2H), 1.97(d, J=12.17Hz, 2H), 1.84(m, 2H), 1.19(t, J=7.00Hz, 3H); MS(M+1)=394.4 |
| 158 | ~N—CH$_2$—CH(CH$_3$)(R)—CH$_2$OH~ | (S)-(+)-3-bromo-2-methyl-1-propanol | 8.38(d, J=6.23Hz, 2H), 8.17(s, 1H), 7.27(m, 2H), 7.15(d, J=6.18Hz, 2H), 7.02(m, 2H), 6.15(d, J=2.93Hz, 1H), 3.65(m, 1H), 3.49(t, J=10.41Hz, 1H), 3.33(d, J=10.42Hz, 1H), 2.97(d, J=11.80Hz, 1H), 2.63(m, 1H), 2.45(m, 2H), 2.25(m, 1H), 2.16(m, 1H), 2.05~1.90(m, 3H), 1.75(m, 2H), 0.73(d, J=6.75Hz, 3H); MS(M+1)=394.3 |
| 159 | ~N—CH$_2$—CH(CH$_3$)(S)—CH$_2$OH~ | (R)-(−)-3-bromo-2-methyl-1-propanol | 8.38(d, J=6.18Hz, 2H), 8.20(s, 1H), 7.27(m, 2H), 7.15(d, J=6.19Hz, 2H), 7.02(m, 2H), 6.15(d, J=2.85Hz, 1H), 3.65(m, 1H), 3.48(t, J=10.34Hz, 1H), 3.32(m, 1H), 2.97(d, J=11.35Hz, 1H), 2.63(m, 1H), 2.45(m, 2H), 2.25(m, 1H), 2.16(m, 1H), 2.05~1.90(m, 3H), 1.75(m, 2H), 0.73(d, J=6.83Hz, 3H); MS(M+1)=394.4 |
| 160 | (diisopropylidene galactopyranose structure) | 6-deoxy-1,2:3,4-di-o-isopropylidene-6-iodo-α-D-galactopyranose | 5.55(d, J=5.13Hz, 1H), 4.58(m, 1H), 4.29(m, 1H), 4.20(m, 1H), 3.98(m, 1H), 2.71(m, 1H), 2.61(m, 1H), 1.53(s, 3H), 1.44(s, 3H), 1.33(s, 3H), 1.32(s, 3H) |
| 161 | ~N—CH(CH$_3$)—CH$_2$—CO$_2$CH$_3$~ | Methyl 3-bromobutyrate | 8.60(s, 1H), 8.38(d, J=6.06Hz, 2H), 7.28(m, 2H), 7.15(d, J=6.23Hz, 2H), 7.02(m, 2H), 6.16(d, J=2.85Hz, 1H), 3.68(s, 3H), 3.39(m, 1H), 3.06(d, J=10.61Hz, 2H), 2.80(m, 1H), 2.67(m, 1H), 2.47(m, 2H), 2.16(m, 1H), 2.35(qt, J=8.46Hz, 1H), 2.02(m, 4H), 1.18(d, J=6.59Hz, 3H); MS(M+1)=422.2 |
| 162 | ~N(CH$_3$)(CH$_2$CH$_2$OH)~ | Ex. 147 + iodomethane | (in CD$_3$OD) 2.2(m, 4H), 3.1(m, 1H), 3.3(s, 3H), 3.6(m, 4H), 3.7(m, 2H), 4.2(m, 2H), 6.7(s, 1H), 7.2(m, 2H), 7.5(m, 2H), 7.7(m, 2H), 8.4(m, 2H) |
| 163 | ~N—CH$_2$CH$_2$CO$_2$CH$_3$~ | Methyl 3-bromo-propionate | (CD$_3$OD) 3.68(s, 3H), 2.74(t, J=7.05Hz, 2H), 2.58(t, J=7.43Hz, 2H) |
| 164 | ~N—CH$_2$CH$_2$CO$_2$H~ | 3-iodo-propionic acid | (CD$_3$OD) 3.34(t, J=6.64Hz, 2H), 2.63(t, J=6.60Hz, 2H) |
| 165 | ~N—CH(CH$_3$)—CO$_2$CH$_3$~ | methyl-2-bromo-propionate | 3.71(s, 3H), 3.35(q, J=7.08Hz, 1H), 1.33(t, J=7.03Hz, 3H) |
| 166 | ~N—CH(S)(CH$_3$)—CO$_2$CH$_3$~ | Methyl (R)-(+)-2-chloro-propionate | 8.38(d, J=6.14Hz, 2H), 8.13(s, 1H), 7.27(m, 2H), 7.16(d, J=6.18Hz, 2H), 7.02(m, 2H), 6.16(d, J=2.92Hz, 1H), 3.71(s, 3H), 3.35(qt, J=7.00Hz, 1H), 3.00(d, J=10.25Hz, 2H), 2.60(m, 1H), 2.41(m, 1H), 1.97(m, 2H), 1.73(m, 2H), 1.32(d, J=7.04Hz, 3H); MS(M+1)=408.3 |

-continued

| Ex. | N—R | Alkyl halide | NMR (CDCl₃) |
| --- | --- | --- | --- |
| 167 | N(R)-CH(CH₃)-CO₂CH₃ | Methyl (S)-(−)-2-chloro-propionate | 3.71(s, 3H), 3.35(qt, J=7.00Hz, 1H), 1.32(d, J=7.04Hz, 3H) |
| 168 | N-C(CH₃)₂-CO₂CH₃ | Methyl α-bromo-isobutyrate | 3.71(s, 3H), 1.36(s, 6H) |
| 169 | N-CH₂-C(O)-C₆H₄-Cl | 2-bromo-4'-chloro-acetophenoe | 3.98(m, 2H), 7.40(d, J=8.7Hz, 2H), 7.86(d, J=8.5Hz, 2H). |
| 170 | N-CH₂-C(O)-C₆H₄-Br | 2,4'-dibromo-acetophenone | 3.85(m, 2H), 7.53(d, J=8.6Hz, 2H), 7.75(d, J=8.6Hz, 2H). |
| 171 | N-CH₂-C(O)-C₆H₄-OCHF₂ | 2-bromo-4'-(difluoro-methoxy)-acetophenone | 3.46(s, 1H), 3.80(s, 2H), 7.18(m, 2H), 8.38(m, 2H). |
| 172 | N-CH₂-C(O)-C₆H₄-OCF₃ | 2-bromo-4'-(trifluoro-methoxy)-acetophenone | 3.80(s, 2H), 7.28(m, 2H), 8.38(m, 2H). |
| 173 | N-CH₂-C(O)-C₆H₄-F | 2-bromo-4'-fluoroaceto-phenone | 1.9(m, 2H), 2.0(m, 2H), 2.3(m, 2H), 2.6(m, 1H), 3.1(m, 2H), 3.8(s, 2H), 6.2(s, 1H), 7.0(m, 2H), 7.2(m, 4H), 7.3(m, 2H), 8.1(m, 2H), 8.4(m, 2H) |
| 174 | N-CH₂-C(O)-C₆H₄-OCH₃ | 2-bromo-4'-methoxyaceto-phenone | 1.8(m, 2H), 2.0(m, 3H), 2.6(m, 1H), 2.8(m, 1H), 3.2(m, 2H), 3.9(s, 3H), 4.0(s, 2H), 6.2(s, 1H), 6.9(m, 2H), 7.0(m, 2H), 7.2(m, 4H), 7.3(m, 2H), 8.0(m, 2H), 8.2(broad, 1H), 8.4(m, 2H) |
| 175 | N-CH₂-CH(OH)-C₆H₄-NO₂ | 2-bromo-3'-nitroaceto-phenone | 1.8(m, 2H), 2.0(m, 2H), 2.4(m, 2H), 2.6(m, 1H), 3.1(m, 1H), 3.8(m, 2H), 6.2(s, 1H), 7.0(m, 2H), 7.2(m, 2H), 7.3(m, 2H), 7.6(m, 1H), 8.4(m, 5H), 8.9(s, 1H) |

| Ex. | N—R | Alkyl halide | NMR (CDCl$_3$) |
|---|---|---|---|
| 176 | N-CH$_2$-C(O)-C$_6$H$_4$-CH$_3$ (4-) | 2-bromo-4'-methyl acetophenone | 2.0(m, 4H), 2.4(s, 3H), 2.4(m, 2H), 2.7(m, 1H), 3.2(m, 2H), 3.9(s, 2H), 6.2(d, 1H), 7.0(m, 2H), 7.2(m, 6H), 7.9(m, 2H), 8.4(m, 2H) |
| 177 | N-CH$_2$-C(O)-C$_6$H$_4$-N$_3$ (4-) | 2-bromo-4'-azidoacetophenone | (+CD$_3$OD) 2.0(m, 4H), 2.3(m, 2H), 2.6(m, 1H), 3.1(m, 2H), 3.9(s, 2H), 6.2(s, 1H), 7.0(m, 2H), 7.2(m, 6H), 7.9(m, 2H), 8.4(m, 2H) |
| 178 | N-CH$_2$-C(O)-C$_6$H$_4$-CF$_3$ (4-) | 2-bromo-4'-trifluoromethylacetophenone | 1.9(m, 2H), 2.0(m, 2H), 2.4(m, 2H), 2.6(m, 1H), 3.1(m, 2H), 3.9(s, 2H), 6.2(d, 1H), 7.0(m, 2H), 7.2(m, 4H), 7.7(m, 2H), 8.1(m, 2H), 8.4(m, 2H) |
| 179 | N-CH$_2$-C(O)-C$_6$H$_4$-N(Et)$_2$ (4-) | 2-bromo-4'-diethylaminoacetophenone | 1.2(t, 6H), 2.0(m, 4H), 2.5(m, 2H), 2.7(m, 1H), 3.2(m, 2H), 3.4(m, 5H), 3.8(s, 2H), 6.2(d, 1H), 6.6(m, 2H), 7.0(m, 2H), 7.2(m, 4H), 7.3(m, 2H), 8.0(m, 2H), 8.2(broad, 1H), 8.4(m, 2H) |
| 180 | N-CH$_2$-C(O)-C$_6$H$_4$-n-C$_5$H$_{11}$ (4-) | 2-bromo-4'-pentylacetophenone | 0.9(t, 3H), 1.4(m, 4H), 1.6(m, 2H), 2.0(m, 4H), 2.5(m, 1H), 2.7(m, 2H), 3.2(m, 2H), 3.9(s, 2H), 6.2(d, 1H), 7.0(m, 2H), 7.2(m, 2H), 7.3(m, 4H), 8.0(m, 2H), 8.2(broad, 1H), 8.4(m, 2H) |

The following compounds were prepared using the general procedure for reduction of ketones. The ketone starting material was dissolved in methanol and tetrahydrofuran, and sodium borohydride was added thereto. The reaction mixture was stirred at room temperature overnight, then separated by preparative TLC (methanol/dichloromethane 8:92) to provide the desired hydrxoy compound.

| Ex. | N—R | Ketone | NMR |
|---|---|---|---|
| 181 | N-CH$_2$-CH(OH)-C$_6$H$_4$-OCF$_3$ (4-) | Ex. 172 | 2.52(m, 2H), 4.78(m, 1), 7.18(m, 2H), 7.37(d, J=6.9Hz, 2H). |
| 182 | N-CH$_2$-CH(OH)-C$_6$H$_4$-OCHF$_2$ (4-) | Ex. 172 | 2.51(m, 2H), 4.78(m, 1H), 7.17(d, J=6.3Hz, 2H), 7.34(d, J-6.6Hz, 2H). |

-continued

| Ex. | N—R | Ketone | NMR |
|---|---|---|---|
| 183 | 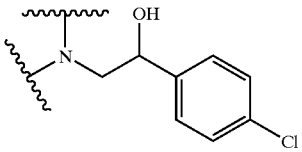 | Ex. 169 | 4.95(bs, 1H), 7.30(m, 4H). |
| 184 | 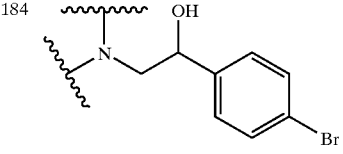 | Ex. 170 | 4.82(bs, 1H), 7.25(m, 4H). |
| 185 | 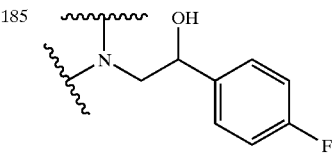 | Ex. 173 | (+CD$_3$OD) 1.8(m, 2H), 2.0(m, 2H), 2.2(m, 1H), 2.5(m, 4H), 3.0(m, 1H), 3.2(m, 1H), 4.8(m, 1H), 6.1(s, 1H), 7.0(m, 4H), 7.2(m, 2H), 7.3(m, 4H), 8.2(m, 2H) |
| 186 | 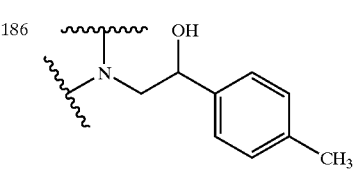 | Ex. 176 | (+CD$_3$OD) 1.8–2.6(m, 9H), 2.3(s, 3H), 3.3(m, 2H), 4.8(m, 1H), 6.1(s, 1H), 7.0(m, 2H), 7.2(m, 6H), 7.9(m, 2H), 8.3(m, 2H) |
| 187 | 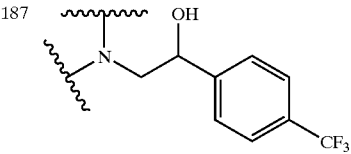 | Ex. 178 | 1.8(m, 2H), 2.0(m, 2H), 2.1(m, 1H), 2.2(m, 1H), 2.5(m, 2H), 3.0(m, 1H), 3.2(m, 2H), 4.8(m, 1H), 6.1(s, 1H), 7.0(m, 2H), 7.1(m, 2H), 7.2(m, 2H), 7.4(m, 2H), 7.5(m, 2H), 8.2(m, 2H) |
| 188 | 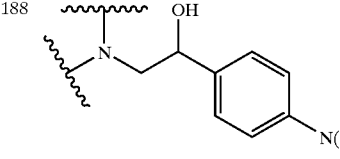 | Ex. 179 | (+CD$_3$OD) 1.2(m, 6H), 1.8(m, 2H), 2.0(m, 2H), 2.2(m, 1H), 2.4–2.8(m, 5H), 3.1(m, 1H), 3.4(m, 4H), 4.7(m, 1H), 6.1(s, 1H), 6.6(m, 2H), 7.0(m, 2H), 7.2(m, 4H), 7.3(m, 2H), 8.3(m, 2H) |
| 189 | 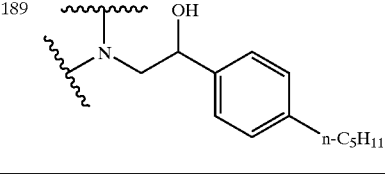 | Ex. 180 | (+CD$_3$OD) 0.9(t, 3H), 1.3(m, 4H), 1.6(m, 2H), 2.0(m, 4H), 2.2(m, 1H), 2.6(m, 4H), 3.0(m, 1H), 3.3(m, 1H), 4.8(s, 1H), 6.2(s, 1H), 7.0(m, 2H), 7.2(m, 4H), 7.3(m, 4H), 8.4(m, 2H) |

The following compounds were prepared using reductive amination by sodium triacetoxy borohydride. To a suspension of the piperidine made in reference example, and acetic acid in anhydrous tetrahydrofuran under nitrogen at room temperature, the appropriate carbonyl compound and sodium triacetoxyborohydride were added slowly. The resulting solution was allowed to stir at room temperature overnight. The crude product was purified by flash silica gel chromatography (MeOH—CH$_2$Cl$_2$, 8:92 v/v containing 1% N$_4$OH) to provide the desired product, after drying

| Ex | N—R | Carbonyl | NMR(CDCl$_3$), MS(M+1) Data |
|---|---|---|---|
| 190 | N—CH(CH$_3$)CH$_2$OCH$_3$ | Methoxyacetone | 3.50(m, 1H), 3.36(s, 3H), 3.34(m, 1H), 3.86(m, 1H); MS(M+1)=394.3 |
| 191 | N-(2-methyltetrahydrofuran-3-yl) | 2-methyltetra-hydrofuran-3-one | 4.12(qn, J=6.22Hz, 1H), 3.99(m, 1H), 3.80(q, J=3.87Hz, 1H), 2.80(m, 1H), 1.95(m, overlapping, 2H), 1.13(d, J=6.31Hz, 3H); MS(M+1)=406.4 |
| 192 | N-(5-oxo-2,5-dihydrofuran-3-yl) | Tetronic acid | 8.66(s, br, 1H), 8.40(d, J=5.98Hz, 2H), 7.31(m, 2H), 7.20(d, J=6.04Hz, 2H), 7.05(m, 2H), 6.20(s, 1H), 4.74(s, 2H), 4.70(s, 1H), 3.16(m, 2H), 2.92(m, 1H), 2.10(m, 2H), 1.80(m, 4H); MS(M+1)=404.3 |
| 193 | N-(tetrahydro-2H-pyran-4-yl) | tetrahydro-4H-pyran-4-one | 4.03(m, 2H), 3.40(m, 2H), 2.65(m, 1H), 1.80(m, 2H), 1.65(m, 2H); MS(M+1)=406.3 |
| 194 | N-(tetrahydrothiophen-3-yl) | tetrahydrothiophen-3-one | 3.67(m, 1H), 2.95(m, 2H), 2.82(m, 4H); MS(M+1)=408.2 |
| 195 | N-(tetrahydro-2H-pyran-3-yl) | Dihydropyran-3-one | 8.70(s, br, 1H), 8.38(d, J=5.98Hz, 2H), 7.30(m, 2H), 7.17(d, J=6.06Hz, 2H), 7.02(m, 2H), 6.15(s, 1H); MS(M+1)=406.3 |
| 196 | N—CH(CH$_3$)CH$_2$OPh | Phenoxy-2-propane | 7.26(m, overlapping, 2H), 6.92(m, 3H), 4.08(m, 1H), 3.90(m, 1H), 3.05(m, overlapping, 1H), 1.19(d, J=6.72Hz, 3H); MS(M+1)=456.3 |
| 197 | N—CH(CH$_2$OH)$_2$ | 1,3-dihydroxy-acetone | 2.66(m, 1H), 3.70(m, 4H). |

| Ex | N—R | Carbonyl | NMR(CDCl₃), MS(M+1) Data |
|---|---|---|---|
| 198 | 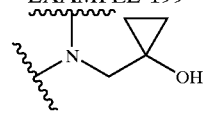 | 2,5-dimethoxy-3-tetrahydrofuran-carboxaldehyde | (CD₃OD) 8.25(d, J=6.18Hz, 2H), 7.35(m, 2H), 7.25(d, J=6.32Hz, 2H), 7.09(m, 2H), 6.19(s, 1H), 5.07(m, 1H), 4.87(m, 1H), 3.39(s, 3H), 3.36(s, 3H), 3.34(d, J=6.91Hz, 2H), 3.09(m, 2H), 2.7~2.3(m, 4H), 2.14(m, 2H), 1.98(m, 2H), 1.80(m, 2H); MS(ESI)=466.3 |

EXAMPLE 199

Step 1 2-(4-Fluorophenyl)-3-(4-pyridinyl)-5-[N-(1-hyroxy-1-cyclopropyl-carbonyl)-4-piperidinyl)pyrrole (1)

Triethylamine (348 μL, 2.49 mmol) was added to a suspension of the compound of reference example (200 mg, 0.622 mmol), 1-hydroxy-1-cyclopropane-carboxylic acid (95.3 mg, 0.933 mmol), and PyBOP (340 mg, 0.653 mmol) in dichloromethane (5 mL). The reaction mixture was stirred at room temperature overnight, and the solution was evaporated to dryness. The residue was purified by preparative TLC (CH₂Cl₂—MeOH, 90:10) to give the desired product (224 mg, not pure). This material was used directly in the next experiment without further purification.

Step 2 2-(4-Fluorophenyl)-3-(4-pyridinyl)-5-[N-(1-hyroxy-1-cyclopropyl-methyl)-4-piperidinyl)pyrrole Borane-methyl sulfide complex (1.68 mL, 2.0 M solution in THF) was added drop wise to stirred solution of the product of Step 1 (224 mg) in dry THF (5 mL) under nitrogen. After 16 h at room temperature, the solution was cooled, and excess borane was quenched with methanol. The solvent was evaporated to dryness, and the residue was dissolved in THF (5 mL). 2-(Dimethylamino)ethanol (0.67 mL) was added, and the reaction mixture was heated under reflux for 3 h, cooled, and evaporated to dryness. The residue was purified by preparative TLC (CH₂Cl₂—MeOH, 90:10) to give the title compound (50 mg). NMR (CD₃OD): 0.54–0.59 (m, 2H, cyclopropyl),0.75–0.77 (m, 2H, cyclopropyl),1.85, 2.02, 2.32, 2.61 (4 m, 8H, piperidinyl), 2.64–2.69 (m, 1H, CH),3.26–3.29 (d, 2H, CH2),6.20 (s, 1H, H-4),7.08–7.11 (m, 2H, H-2 & H-6 of 4-F-phenyl), 7.24–7.26 (m, 2H, H-2 & H-6 of pyridinyl),7.33–7.37 (m, 2H, H-3 & H-5 of 4-F-phenyl),8.24–8.26 (m, 2H, H-3 & H-5 of pyridinyl)

EXAMPLE 201

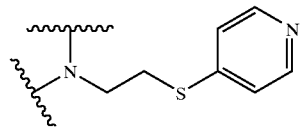

Step 1. 4-(Pyridylthio)acetic acid (169 mg, 1 mmole) was suspended in CH₂Cl₂ (10 mL) at ambient temperature and HOAT (200 mg, 1.45 mmoles) and triethylamine (350 uL, 286 mg, 2.2 mmoles) and the compound of reference example (321 mg, 1 mmole) were added. Then EDC (440 mg, 2.3 mmoles) was also added. The mixture was stirred overnight and brine and CH₂Cl₂ were added separate organic layer dried and concentrated. Chromatography on Flash 40 using 9:1 CH2Cl2/Methanol as eluent yielded product (140 mg).

Step 2: The amide of Step 1 (118 mg, 0.25 mmoles) was dissolved in THF (5 mL) and BH₃CH₃SCH₃ (2.0 mL of 2M, 4 mmoles) was added. The mixture was stirred for 18 hr and concentrated to dryness Prep TLC using 9:1 CH2Cl2/Methanol as eluent gave product (60 mg). Reduction of the amide obtained above could also be done with lithium aluminum hydride in THF or BH3-THF.NMR (CD₃OD) 1.78–3.27(m,12H) 6.19 (s, pyrrole), 7.09–7.11 (m, F-Ar 2H) 7.24–7.25, 7.31–7.33 (m, 2H Pyr), 7.33–7.36(m, 6H Ar), 8.24–8.26, 8.30–8.31 (m, 2H Pyr)

The following compounds were prepared according to the procedure described in Example 201 (Steps 1 and 2):

| Ex. | N—R | Reagent | NMR |
|---|---|---|---|
| 200 | | 3,3-dicyclopropyl-3-hydroxypropionic acid | (CD₃OD): 0.31–0.39(m, 4H, cyclopropylCH2), 0.40–0.45 (m, 4H, cyclopropylCH2), 0.81–0.85(m, 2H, cyclopropylCH), 1.70–1.73, 2.01–2.04, 2.12–2.17, 3.10–3.12(4 m, 8H, piperidinyl), 1.79 & 2.77(2t, 4H, NCH2CH2), 6.18(s, 1H, H-4), 7.07–7.11(m, 2H, H-2 & H-6 of 4-F-phenyl), 7.24–7.25 (m, 2H, H-2 & H-6 of pyridinyl), 7.33–7.36(m, 2H, H-3 & H-5 of 4-F-phenyl), 8.24–8.25(m, 2H, H-3 & H-5 of pyridinyl) |

| Ex. | N—R | Reagent | NMR |
|---|---|---|---|
| 202 | (N-C(=O)-CH2CH2-OCH3) | 3-methoxy-propionic acid | 2.56(t, J=6.4Hz, 2H), 3.32(s, 3H), 3.67(t, J=6.6Hz, 2H). |
| 203 | (N-CH2CH2CH2-OCH3) | Ex. 202 | 1.78(m, 2H), 2.43(t, J=7.8Hz, 2H), 3.32(s, 3H), 3.43(t, J=6.4Hz, 2H). |
| 204 | (N-C(=O)-CH2-O-C6H4-OH) | O-(4-hydroxy-phenyl)glycolic acid | (+CD3OD 3.2(m, 1H), 4.1(m, 1H), 4.6AB, 2H), 6.2(s, 1H) M+1: 472.2 |
| 205 | (N-CH2CH2-O-C6H4-OH) | Ex. 204 | 2.9(t, 2H), 3.2(m, 2H), 4.1(t, 2H), 6.2(s, 1H) M+1: 458.3 |
| 206 | (N-C(=O)-CH2CH2-O-C6H4-OH) | O-(4-hydroxy-phenyl)lactic acid | (+CD3OD) 1.5(m, 3H), 4.8(m, 1H), 6.0 & 6.2(2s, 1H) M+1: 486.2 |
| 207 | (N-CH2CH2CH2-O-C6H4-OH) | Ex. 206 | 1.3(m, 3H), 3.2(m, 2H), 3.7(m, 1H), 4.5(m, 1H), 6.2(m, 1H) M+1: 472.3 |
| 208 | (N-C(=O)-CH(OH)-CH2-imidazolyl) | 2-hydroxy-3-(4-imidazolyl)-propanoic acid | 3.0(m, 2H), 4.6(m, 1H), 6.9(m, 1H), 7.5(m, 1). |

What is claimed is:

1. A compound having the formula I:

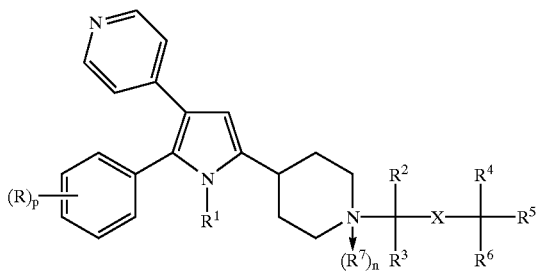

I or a physiologically acceptable salt thereof, wherein n is 0 or 1;
m is 0, 1 or 2;
p is 1, 2 or 3;

X is
  (1) a bond,
  (2) $(CR^aR^a)_p$,
  (3) $C_{3-7}$ cycloalkylene, or
  (4) $C_{3-7}$ cycloalkylidene;

R is halogen;

$R^1$ is
  (1) hydrogen or
  (2) $C_{1-6}$ alkyl;

$R^2$ and $R^3$ are independently selected from
  (1) hydrogen,
  (2) $C_{1-6}$ alkyl optionally substituted with $OR^b$,
  (3) $C_{2-6}$ alkenyl,
  (4) $C_{2-6}$ alkynyl,
  (5) phenyl optionally substitued with $OR^b$,
  (6) benzyl optionally substitued with $OR^b$,
  (7) $CO_2R^b$; or $R^2+R^3$ represent =O; or when X is a bond or $(CR^aR^a)_p$, $R^2$ and $R^4$ together complete a 4- to 7-membered non-aromatic ring containing 1 or 2 heteroatoms independently selected from O and $S(O)_m$, and said ring being optionally substituted with 1 to 5 groups independently selected from oxo, $OR^b$, $CH_2OR^b$, $CH_2OC(O)R^b$ and $C_{1-6}$alkyl; or when X is a bond or $(CR^aR^a)_p$, $R^2$ and $R^5$ together complete a 4- to 7-membered non-aromatic ring containing 0 to 2 heteroatoms independently selected from O and $S(O)_m$, said ring being optionally substituted with 1 to 5 groups independently selected from oxo, $OR^b$, $CH_2OR^b$, $CH_2OC(O)R^b$ and $C_{1-6}$alkyl;

$R^4$ is
- (1) $OR^b$,
- (2) $OC(O)R^b$,
- (3) $OC(O)OR^b$,
- (4) $OC(O)(CH_2)_m NR^b R^b$,
- (5) $OSO_2R^b$,
- (6) $S(O)_m R^b$
- (7) $OP(O)(OR^b)_2$, or
- (8) $CO_2R^b$; or $R^4+R^6$ represent =O; or $R^4$, $R^5$ and the carbon atoms to which they are attached form a 3- to 7-membered non-aromatic ring containing 1 or 2 heteroatoms independently selected from O or $S(O)_m$, said ring being optionally substituted with 1 to 5 groups independently selected from oxo, $OR^b$, $CH_2OR^b$, $CH_2OC(O)R^b$ and $C_{1-6}$alkyl; or $R^5$ and $R^6$ are independently selected from
- (1) hydrogen,
- (2) $C_{1-12}$alkyl,
- (3) $C_{2-12}$alkenyl,
- (4) $C_{2-12}$alkynyl,
- (5) $C_{3-7}$cycloalkyl-$(C_{1-6}$alkyl$)_n$,
- (6) mono-, bi- or tricyclic heterocyclyl-$(C_{1-6}$alkyl$)_n$, wherein said heterocyclyl contains 3 to 12 ring atoms 1 to 4 of which are independently selected from O and $S(O)_m$,
- (7) aryl-$(C_{1-6}$alkyl$)_n$,
- (8) heteroaryl-$(C_{1-6}$alkyl$)_n$,
- (9) $CO_2R^b$, or
- (10) $OR^b$, wherein alkyl, alkenyl and alkynyl are optionally substituted with 1 to 5 groups independently selected from $R^c$, cycloalkyl and heterocyclyl are optionally substituted with 1 to 5 groups independently selected from $R^c$, alkyl, and spirofused $C_{3-6}$ cycloalkylidene, and aryl and heteroaryl are optionally substituted with 1 to 3 groups independently selected from $R^d$, or $R^5$, $R^6$ and the carbon atoms to which they are attached form a 3- to 7-membered non-aromatic ring containing 0 to 2 heteroatoms independently selected from O and $S(O)_m$, optionally substituted with 1 to 5 groups independently selected from oxo, $OR^b$, $CH_2OR^b$, $CH_2OC(O)R^b$ and $C_{1-6}$alkyl; or when X is $(CR^aR^a)_p$, $R^5$ and any one of the $R^a$ may together complete a 3- to 7-membered non-aromatic carbocyclic ring;

$R^7$ is
- (1) O or
- (2) methyl;

$R^a$ is
- (1) hydrogen, or
- (2) $C_{1-6}$alkyl, or $R^b$ is
- (1) hydrogen,
- (2) $C_{1-12}$alkyl
- (3) $C_{2-12}$alkenyl,
- (4) $C_{2-12}$alkynyl,
- (5) $C_{3-7}$cycloalkyl-$(C_{1-6}$alkyl$)_n$,
- (6) heterocyclyl-$(C_{1-6}$alkyl$)_n$,
- (7) aryl-$(C_{1-6}$alkyl$)_n$, or
- (8) heteroaryl-$(C_{1-6}$alkyl$)_n$, wherein alkyl, cycloalkyl, heterocyclyl, alkenyl and alkynyl are optionally substituted with up to 5 groups independently selected from $R^c$, and aryl and heteroaryl are optionally substituted with up to 3 groups independently selected from $R^d$, or two $R^b$ groups attached to the same nitrogen atom together complete a 4- to 7-membered ring optionally containing an additional heteroatom selected from O, S and N—Rf;

$R^c$ is
- (1) halogen,
- (2) $S(O)_m R^e$,
- (3) $OR^e$,
- (4) $OC(O)NR^e R^e$,
- (5) $OC(O)OR^e$,
- (6) $OC(O)R^e$,
- (7) $OSO_2 R^e$
- (8) $OCF_3$,
- (9) $CF_3$,
- (10) $C(O)OR^e$
- (11) $C(O)R^e$
- (12) oxo,
- (13) $N_3$,
- (14) CN,
- (15) $NO_2$, or
- (16) $P(O)(OR^e)_2$;

$R^d$ is
- (1) a group selected from $R^c$,
- (2) $C_{1-6}$alkyl optionally substituted with 1 to 6 groups selected from $R^c$,
- (3) aryl optionally substituted with 1 to 3 groups selected from $R^c$,
- (4) heteroaryl optionally substituted with 1 to 3 groups selected from $R^c$,
- (5) $NR^e R^e$,
- (6) $NR^f SO_2 R^e$,
- (7) $NR^f C(O)OR^e$,
- (8) $NR^f C(O) R^e$,
- (9) $NR^f C(O)NR^e R^e$;

$R^e$ is
- (1) hydrogen,
- (2) $C_{1-12}$alkyl optionally substituted with 1 to 5 groups selected from halogen, CN, OH and $C_{1-10}$alkoxy optionally substituted with oxiranyl, hydroxy or $C_{1-6}$ alkyl,
- (3) $C_{2-12}$alkenyl,
- (4) $C_{2-12}$alkynyl,
- (5) $C_{3-7}$cycloalkyl-$(C_{1-6}$alkyl$)_n$,
- (6) aryl$(C_{1-6}$alkyl$)_n$ optionally substituted with $NO_2$, $C_{1-6}$alkyl, $C_{1-6}$alkoxy, or halogen,
- (7) heteroaryl$(C_{1-6}$alkyl$)_n$, or two $R^e$ groups together with the nitrogen atom to which they are attached form a 3- to 7-membered ring optionally containing an additional heteroatom selected from O, S and N—$R^f$;

$R^f$ is
- (1) hydrogen or
- (2) $C_{1-6}$alkyl.

2. A compound of claim 1 wherein R is 4-fluoro.

3. A compound of claim 1 wherein $R^1$ is hydrogen.

4. A compound of claim 1 wherein n of $(R^7)_n$ is 0.

5. A compound of claim 1 wherein $R^3$ is hydrogen, and $R^2$ is hydrogen, methyl, hydroxy methyl, $C_{1-3}$alkoxy methyl, phenyl, or $C_{1-3}$alkoxyphenyl; or when X is a bond or $(CR^aR^a)_p$, $R^2$ and $R^4$ together complete a 4- to 7-membered non-aromatic ring containing 1 or 2 heteroatoms independently selected from O and S(O)m, and said ring being optionally substituted with 1 to 5 groups independently selected from oxo, $OR^b$, $CH_2OR^b$, and $C_{1-6}$alkyl; or when X is a bond or $(CR^aR^a)_p$, $R^2$ and $R^5$ together complete a 4- to 7-membered non-aromatic ring containing 0 to 2 heteroatoms independently selected from O and $S(O)_m$, said ring being optionally substituted with 1 to 5 groups independently selected from oxo, $OR^b$, $CH_2OR^b$, and $C_{1-6}$alkyl.

6. A compound of claim 1 wherein X is a bond, $(CR^aR^a)_p$ wherein p is 1 or 2, or $C_{3-6}$cycloalkylene.

7. A compound of claim 1 wherein $R^4$ is $OR^b$, or $R^4$ and $R^6$ together represent oxo, or $R^4$, $R^5$ and the carbon atoms to which they are attached form a 3- to 7-membered non-aromatic ring containing 1 or 2 heteroatoms independently selected from O or $S(O)_m$, said ring being optionally substituted with 1 to 5 groups independently selected from oxo, $OR^b$, $CH_2OR^b$, and $C_{1-6}$alkyl.

8. A compound of claim 1 wherein $R^5$ and $R^6$ are each hydrogen or $C_{1-12}$ alkyl optionally substituted with 1 to 5 groups independently selected from $R^c$; or $R^6$ is hydrogen and $R^5$ is selected from $C_{1-12}$alkyl, $C_{3-6}$cycloalkyl-$(C_{1-3}$alkyl$)_n$, heterocyclyl-$(C_{1-3}$alkyl$)_n$, wherein said heterocyclyl contains 3 to 6 ring atoms 1 to 2 of which are independently selected from O and $S(O)_m$, aryl-$(C_{1-3}$alkyl$)_n$, heteroaryl-$(C_{1-3}$alkyl$)_n$, $CO_2R^b$, and $OR^b$, wherein alkyl, alkenyl and alkynyl are optionally substituted with 1 to 5 groups independently selected from $R^c$, cycloalkyl and heterocyclyl are optionally substituted with 1 to 5 groups independently selected from $R^c$ and alkyl, and aryl and heteroaryl are optionally substituted with 1 to 3 groups independently selected from $R^d$; or $R^5$, $R^6$ and the carbon atoms to which they are attached form a 3- to 7-membered non-aromatic ring containing 0 to 2 heteroatoms independently selected from O and $S(O)_m$, optionally substituted with 1 to 5 groups independently selected from oxo, $OR^b$, $CH_2OR^b$, and $C_{1-6}$alkyl; or when X is $(CR^aR^a)_p$, $R^5$ and any one of the $R^a$ may together complete a 3- to 7-membered non-aromatic carbocyclic ring.

9. A compound of claim 1 having the formula Ia:

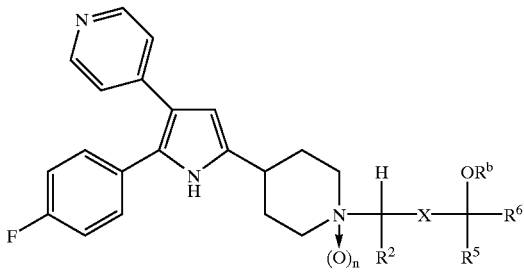

Ia wherein n, X, $R^2$, $R^5$, $R^6$ and $R^b$ are as defined in claim 1.

10. A compound of claim 9 wherein $R^2$ is hydrogen, $C_{1-3}$alkyl optionally substituted with hydroxy or $C_{1-3}$alkoxy, or phenyl optionally substituted with $C_{1-3}$alkoxy.

11. A compound of claim 9 wherein X is a bond, $(CR^aR^a)_p$ or $C_{3-6}$alkylene in which $R^a$ is H or $C_{1-3}$ alkyl, and p is 1 or 2.

12. A compound of claim 9 wherein $R^5$ is hydrogen, $C_{1-6}$alkyl, $CO_2R^b$, aryl, heteroaryl, or heterocyclyl wherein alkyl, aryl, heteroaryl and heterocyclyl are optionally substituted with 1 to 5 groups selected from $OR^b$ and halogen, or $R^5$, $R^6$ and the carbon atom to which they are attached for a $C_{3-6}$ carbocyclic ring, or when X is a bond or $(CR^aR^a)_p$, $R^5$ and $R^2$ together complete a 4- to 5-membered non-aromatic ring containing 0 or 1 heteroatom selected from O and $S(O)_m$, or when X is $(CR^aR^a)_p$, $R^5$ and one of the $R^a$ together complete a 3- to 6-memebered carbocyclic ring.

13. A compound of claim 9 having the formula Ib:

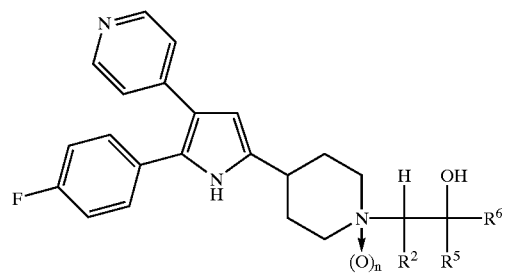

Ib wherein $R^6$ is hydrogen, $R^5$ is $C_{1-6}$ alkyl, $C_{2-10}$alkenyl, $CO_2R^b$, aryl, heteroaryl or heterocyclyl wherein alkyl, alkenyl, aryl, heteroaryl and heterocyclyl are optionally substituted with 1 or 2 groups selected from $OR^b$ and halogen, or $R^5$, $R^6$ and the carbon atom to which they are attached form a $C_{3-6}$ carbocyclic ring, or $R^5$ and $R^2$ together complete a 4- to 5-membered non-aromatic ring containing 0 or 1 heteroatom selected from O and $S(O)_m$.

14. A compound of claim 13 wherein $R^5$ is selected from (1) $C_{1-6}$ alkyl optionally substituted with 1 or 2 groups selected from (a) hydroxy, (b) $C_{1-10}$alkoxy optionally substituted with 1 to 10 halogen atoms or cyano, (c) $C_{3-6}$alkenyloxy, (d) heteroaryl-$C_{1-3}$alkoxy, (e) phenoxy optionally substituted with 1 or 2 groups selected from nitro, $C_{1-5}$alkoxy, halogen, and $C_{1-5}$alkyl, (f) benzyloxy, and (g) halogen (2) $CO_2$—$C_{1-3}$alkyl, (3) $C_{2-10}$alkenyl, and (4) phenyl optionally substituted with 1 or 2 groups selected from (a) nitro, (b) $C_{1-5}$alkoxy optionally substituted with 1 to 5 halogen atoms, (c) halogen, (d) amino, (e) mono-$C_{1-5}$alkylamine, (f) di-$C_{1-5}$alkylamine, (g) trifluoromethyl, and (h) $C_{1-5}$alkyl.

15. A compound of claim 13 wherein $R^2$ and $R^5$ together complete a 4- to 7-membered non-aromatic ring containing 0 to 2 heteroatoms independently selected from O and $S(O)_m$, said ring being optionally substituted with 1 to 5 groups independently selected from oxo, $OR^b$, $CH_2OR^b$, $CH_2OC(O)R^b$ and $C_{1-6}$alkyl.

16. A method for the treatment or prevention of protozoal diseases comprising administering to a host in need of such treatment a therapeutically effective amount of a compound of claim 1.

17. A method for the treatment or prevention of coccidiosis in poultry comprising administering to the poultry a therapeutically effective amount of a compound of claim 1.

18. A pharmaceutical composition comprising a compound of claim 1 and an inert carrier.

19. A composition for the treatment or prevention of coccidiosis in poultry comprising a therapeutically effective amount of a compound of claim 1 in poultry feedstuff.

20. A composition of claim 19 wherein said second anticoccidial agent is selected from amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril.

21. A composition of claim 19 wherein said second anticoccidial agent is selected from the group consisting of amprolium, ethopabate, lasalocid, monensin, salinomycin, and diclazuril.

* * * * *